US008703194B2

(12) United States Patent
Liu et al.

(10) Patent No.: US 8,703,194 B2
(45) Date of Patent: Apr. 22, 2014

(54) STIMULUS-RESPONSIVE BIODEGRADABLE POLYMERS AND METHODS OF PREPARATION

(75) Inventors: Ye Liu, Singapore (SG); Decheng Wu, Singapore (SG); Chaobin He, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 1333 days.

(21) Appl. No.: 11/934,638

(22) Filed: Nov. 2, 2007

(65) Prior Publication Data
US 2009/0123544 A1 May 14, 2009

(51) Int. Cl.
*A61K 9/14* (2006.01)
(52) U.S. Cl.
USPC ............................ 424/484; 424/486; 424/485
(58) Field of Classification Search
USPC .......................................... 424/484, 485, 486
See application file for complete search history.

(56) References Cited

U.S. PATENT DOCUMENTS

| 6,784,266 B2 | 8/2004 | Kim et al. |
| 2004/0247670 A1 | 12/2004 | Hennink et al. |
| 2004/0260115 A1 | 12/2004 | Liu et al. |
| 2005/0169882 A1 | 8/2005 | Lowe et al. |
| 2005/0277739 A1 | 12/2005 | Yang et al. |
| 2006/0105001 A1 | 5/2006 | Cubicciotti |
| 2009/0022683 A1 | 1/2009 | Song et al. |

FOREIGN PATENT DOCUMENTS

| JP | 11322941 A | 11/1999 |
| JP | 2005-532323 | 10/2005 |
| KR | 10-2007-0076386 | 7/2007 |
| WO | WO 95/24430 A2 | 9/1995 |
| WO | WO 01/87227 A2 | 11/2001 |
| WO | 03/097107 | 11/2003 |
| WO | WO 2004/072258 A2 | 8/2004 |
| WO | 2006/098547 | 9/2006 |
| WO | 2006/109945 | 10/2006 |

OTHER PUBLICATIONS

Wu et al., "Novel thermo-sensitive membranes prepared by rapid bulk photo-grafting polymerization of N,N-diethylacrylamide onto the microfiltration membranes of Nylon," J. Membrane Sci. 283 (2006) 13-20.*

Chen et al., J. Biomater. Sci. Polymer Edn, vol. 5, No. 4, pp. 371-382 (1994).*
National University of Singapore Department of Bioengineering Final Year Project listing, http://www.bioeng.nus.edu.eg/stu/file/fyp-proj-ist-0708.pdf, published Jun. 2007.
Jeong, B. and Gutowska, A., "Lessons from nature: stimuli-responsive polymers and their biomedical applications", Trends in Biotechnology, Jul. 1, 2002, pp. 305-311, vol. 20, Issue 7.
Roy, I. and Gupta, M. N., "Smart Polymeric Materials: Emerging Biochemical Applications", Chemistry & Biology, Dec. 2003, pp. 1161-1171, vol. 10, Issue 12.
Qui, Y. and Park, K., "Environment-sensitive hydrogels for drug delivery", Advanced Drug Delivery Reviews, Dec. 31, 2001, pp. 321-339, vol. 53, Issue 3.
Schmaljohann, D., "Thermo- and pH-responsive polymers in drug delivery", Advanced Drug Delivery Reviews, Dec. 30, 2006, pp. 1655-1670, vol. 58, Issue 15.
Gil, E.S. and Hudson, S.M., "Stimuli-responsive polymers and their bioconjugates", Progress in Polymer Science, Dec. 2004, pp. 1173-1222, vol. 29, Issue 12.
Kamath, K.R. and Park, K., "Biodegradable hydrogels in drug delivery", Advanced Drug Delivery Reviews, Jul.-Aug. 1993, pp. 59-84, vol. 11, Issues 1-2.
Kajiwara, K. and Ross-Murphy, S.B., "Synthetic gels on the move", Nature, Jan. 16, 1992, pp. 208-209, vol. 355, No. 6357.
Osada, Y. et al., "A polymer gel with electrically driven motility", Nature, Jan. 16, 1992, pp. 242-244, vol. 355, No. 6357.
Osada, Y. and Hasebe, M., "Electrically activated mechanochemical devices using polyelectrolyte gels", Chemistry Letters, 1985, pp. 1285-1288, vol. 14, No. 9.
Chen, J.P. et al., "Immobilization of •-Amylase to a Composite Temperature-Sensitive Membrane for Starch Hydrolysis", Biotechnology Progress, Jun. 1998, pp. 473-478, Vol.
Park, C.H. and Orozco-Avila, O., "Concentrating Cellulase from Fermented Broth Using a Temperature-Sensitive Hydrogel", Biotechnology Progress, Nov. 1992, pp. 521-526.
1st Office Action issued in corresponding JP Application No. 2007-310911 (dated Sep. 11, 2012).
Office Action issued in corresponding Korean Application No. 10-2007-0123635 (dated Jan. 21, 2014).
Lin et al., "Linear poly(amido amine)s with secondary and tertiary amino groups and variable amounts of disulfide linkages: Synethesis and in vitro gene transfer properties", Journal of Controlled Release 116 (2006) 130-137.

* cited by examiner

Primary Examiner — Michael G Hartley
Assistant Examiner — Robert Cabral
(74) Attorney, Agent, or Firm — Klarquist Sparkman, LLP

(57) ABSTRACT

There is presently provided a stimulus-responsive polymer comprising a biodegradable polymer backbone and a stimulus-responsive pendant group attached to the biodegradable polymer backbone, wherein the biodegradable polymer backbone comprises a poly(amino ester) or a poly(amido amine), the poly(amido amine) optionally comprising a disulfide linkage in the backbone.

14 Claims, 13 Drawing Sheets

STIMULUS-RESPONSIVE BIODEGRADABLE POLYMERS AND METHODS OF PREPARATION

FIELD OF THE INVENTION

The present invention relates generally to stimulus-responsive biodegradable polymers, which are useful for biological applications including delivery of bioactive agents.

BACKGROUND OF THE INVENTION

Stimulus-responsive polymers are defined as polymers that undergo change in physical or chemical properties in response to small external change in an environmental parameter, for example pH, temperature or light. Stimulus-responsive polymers are also referred to as stimulus-sensitive, intelligent, smart, or environmentally-sensitive polymers.

Stimulus-responsive polymers have received increased attention due to their potential in various biological applications, including medical applications. Stimulus-responsive polymers have been designed to form various types of polymer assemblies, including cross-linked hydrogels, reversible hydrogels, micelles, modified interfaces and conjugated solutions. Application of these polymers in delivery of therapeutics, tissue engineering, bio-separation techniques, or as sensors or actuators has been reported, indicating the rapid progress of this field of research (Jeong et al. *Trends. Biotechnol.,* 2002, 20, 305; Roy et al. *Chemistry & Biology,* 2003, 10, 1161; US 2006/0105001; US 2005/0169882; WO 2004/072258).

Response to stimulus is a basic process of living systems. Certain environmental conditions are seen in particular locales within the body, such as low pH and elevated temperature (Qiu et al. *Adv. Drug. Deliv. Rev.,* 2001, 53, 321). Research has focussed on temperature and pH sensitive polymers, given that temperature and pH are relatively convenient and effective, as well as biologically relevant, stimuli.

Thus, pH and/or temperature sensitive polymers can be utilised for the preparation of 'smart' drug delivery systems that exploit variations in biological temperature and pH in order to effect site-specific controlled drug release.

Large differences in pH extensively exist in different organs, tissues, and cellular compartments. For example, along the GI tract, the pH changes from acidic in the stomach (pH 2) to more basic in the intestine (pH 5-8). As well, certain cancers, inflamed tissue and wound tissue exhibit a pH different than 7.4, which is the pH of blood circulation. In addition, pH drops from a range of pH 6.0-6.5 within the early endosome to a range of pH 5.0-6.0 within the late endosome and then to a range of pH 4.5-5.0 within the lysosome during cell endocytosis, resulting in a large change in proton concentration inside the various cellular compartments. Therefore, the pH variation within the body can be used to direct the response of a stimulus-responsive polymer when targeted to a particular tissue or cellular compartment. Polycations in non-viral gene therapy, acid triggered drug release systems in cancer targeting and polyanions and amphoteric polymers for endosomolytic delivery are some typical pH responsive polymers investigated in drug delivery (Schmaljohann, D. *Adv. Drug. Deliv. Rev.,* 2006, 58, 1655).

Temperature is the most widely used stimulus in environmentally responsive polymer systems, given that temperature is relatively easy to control and is applicable both in vitro and in vivo. Poly-N-substituted acrylamides, for example poly(N-isopropylacrylamide) (PNIPAAm), polymers based on amphiphilic balance like poly(ethylene oxide)-poly(propylene oxide)-poly(ethylene oxide) (PEO-PPO-PEO), and biopolymers and artificial polypetides like gelatin and agarose are some representative groups of temperature-responsive polymers (Gil et al. *Prog. Polym. Sci.,* 2004, 29, 1173).

PNIPAAm is a commonly investigated stimulus-responsive polymer. This polymer is hydrophilic and soluble in aqueous solution below a lower critical solution temperature (LCST) of approximately 32° C. and becomes hydrophobic and insoluble above the LCST. However, PNIPAAm is not biodegradable, and thus would build up in the body if used for in vivo applications.

Polymers for use in biomedical applications generally require biocompatibility and biodegradability. For example, in drug delivery, biocompatible polymers have relatively low toxicity and biodegradable polymers can enhance sustained drug release and can reduce the need for surgical removal after drug depletion. Thus there still exists a need for development of additional stimulus-responsive polymers that are biocompatible and biodegradable.

SUMMARY OF THE INVENTION

In one aspect, there is provided a stimulus-responsive polymer comprising a biodegradable polymer backbone and a stimulus-responsive pendant group attached to the biodegradable polymer backbone, wherein the biodegradable polymer backbone comprises a poly(amino ester) or a poly(amido amine), the poly(amido amine) optionally comprising a disulfide linkage in the backbone.

In certain embodiments, the biodegradable polymer backbone of the stimulus-responsive polymer comprises at least one secondary amine linkage and at least one tertiary amine linkage prior to attachment of the stimulus-responsive pendant group, and the final stimulus-responsive polymer may comprise at least one secondary amine linkage and at least one tertiary amine linkage.

In particular embodiments, the stimulus-responsive polymer comprises one or more units each independently selected from a unit of formula I:

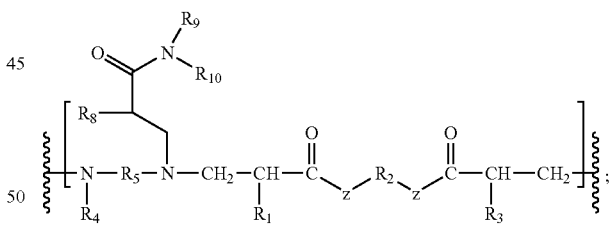

and a unit of formula II:

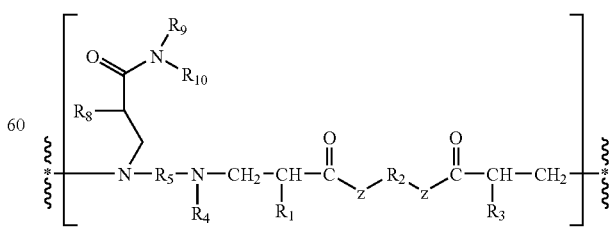

and optionally comprises one or more units, each independently selected from formula III:

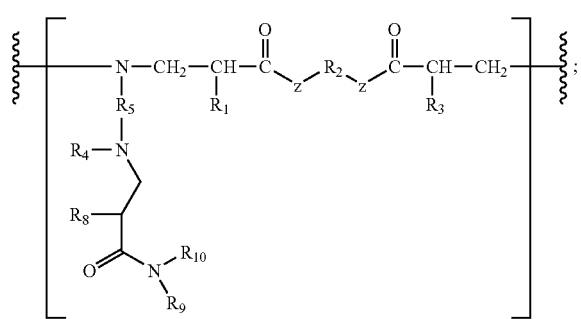

formula IV:

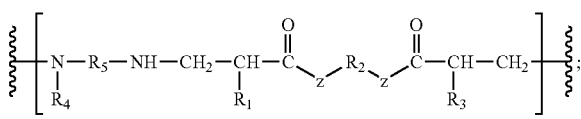

formula V:

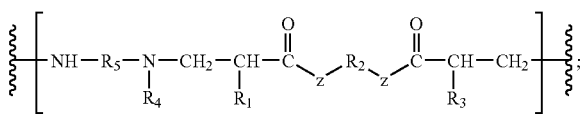

formula VI:

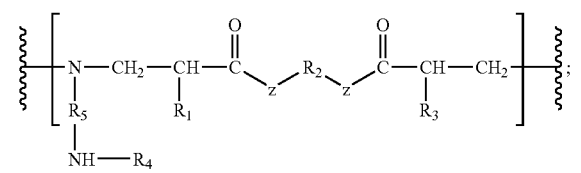

and formula VII:

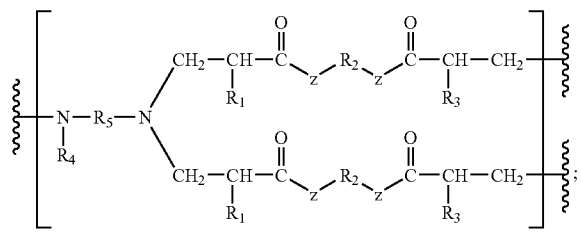

wherein:

z is O or NH;

each of $R_1$, $R_3$ and $R_8$ is independently hydrogen, hydroxyl, halide, thiohydroxyl or hydrocarbyl;

$R_2$ is unsubstituted or substituted $C_{1-30}$ alkylene optionally containing one or more heteroatoms selected from the group consisting of N, O and S; unsubstituted or substituted $C_{2-30}$ alkenylene optionally containing one or more heteroatoms selected from the group consisting of N, O and S; or unsubstituted or substituted $C_{2-30}$ alkynylene optionally containing one or more heteroatoms selected from the group consisting of N, O and S;

$R_5$ is: (i) unsubstituted or substituted $C_{1-30}$ alkylene optionally containing one or more heteroatoms selected from the group consisting of N, O and S; unsubstituted or substituted $C_{2-30}$ alkenylene optionally containing one or more heteroatoms selected from the group consisting of N, O and S; or unsubstituted or substituted $C_{2-30}$ alkynylene optionally containing one or more heteroatoms selected from the group consisting of N, O and S; or (ii) —$R_6$-M-$R_7$—, where $R_6$ is bonded to —N($R_4$)— and is unsubstituted or substituted $C_{1-6}$ alkylene optionally containing one or more heteroatoms selected from the group consisting of N, O and S, or unsubstituted or substituted $C_{2-6}$ alkenylene optionally containing one or more heteroatoms selected from the group consisting of N, O and S; M is CH or N; and $R_7$ is unsubstituted or substituted $C_{1-28}$ alkylene optionally containing one or more heteroatoms selected from the group consisting of N, O and S; unsubstituted or substituted $C_{2-28}$ alkenylene optionally containing one or more heteroatoms selected from the group consisting of N, O and S; or unsubstituted or substituted $C_{2-28}$ alkynylene optionally containing one or more heteroatoms selected from the group consisting of N, O and S;

$R_4$ is: (i) hydrocarbyl; or (ii) when $R_5$ is —$R_6$-M-$R_7$—, $R_4$ is also bonded to M and is unsubstituted or substituted $C_{1-6}$ alkylene optionally containing one or more heteroatoms selected from the group consisting of N, O and S, or unsubstituted or substituted $C_{2-6}$ alkenylene optionally containing one or more heteroatoms selected from the group consisting of N, O and S; and $R_4$, M, $R_6$ and the nitrogen atom to which $R_4$ and $R_6$ are bonded form a saturated or unsaturated four- to twelve-membered heterocyclic ring;

$R_9$ is: (i) unsubstituted or substituted $C_{1-30}$ alkylene optionally containing one or more heteroatoms selected from the group consisting of N, O and S; unsubstituted or substituted $C_{2-30}$ alkenylene optionally containing one or more heteroatoms selected from the group consisting of N, O and S; or unsubstituted or substituted $C_{2-30}$ alkynylene optionally containing one or more heteroatoms selected from the group consisting of N, O and S; or (ii) —$R_{11}$-M-$R_{12}$, where $R_{11}$ is bonded to —N($R_{10}$)— and is unsubstituted or substituted $C_{1-6}$ alkylene optionally containing one or more heteroatoms selected from the group consisting of N, O and S, or unsubstituted or substituted $C_{2-6}$ alkenylene optionally containing one or more heteroatoms selected from the group consisting of N, O and S; M is CH or N; and $R_{12}$ is unsubstituted or substituted $C_{1-28}$ alkyl optionally containing one or more heteroatoms selected from the group consisting of N, O and S; unsubstituted or substituted $C_{2-28}$ alkenyl optionally containing one or more heteroatoms selected from the group consisting of N, O and S; or unsubstituted or substituted $C_{2-28}$ alkynyl optionally containing one or more heteroatoms selected from the group consisting of N, O and S;

$R_{10}$ is (i) hydrocarbyl; or (ii) when $R_9$ is —$R_{11}$-M-$R_{12}$, $R_{10}$ is also bonded to M and is unsubstituted or substituted $C_{1-6}$ alkylene optionally containing one or more heteroatoms selected from the group consisting of N, O and S, or unsubstituted or substituted $C_{2-6}$ alkenylene optionally containing one or more heteroatoms selected from the group consisting of N, O and S; and $R_{10}$, M, $R_{11}$ and the nitrogen atom to which $R_9$ and $R_{11}$ are bonded form a saturated or unsaturated four- to twelve-membered heterocyclic ring;

with the proviso that $R_1$, $R_2$, $R_3$, $R_4$, $R_5$, $R_8$, $R_9$ and $R_{10}$ cannot have a primary amino group, a secondary amino group, or a C=C double bond conjugated with a carbonyl group.

The stimulus-responsive polymer may be responsive to pH, light, temperature or ionic strength.

The stimulus-responsive pendant group may have the structure of formula X:

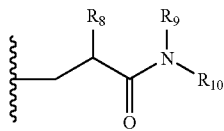

wherein $R_8$, $R_9$ and $R_{10}$ are as defined above.

In certain embodiments, the stimulus-responsive group may be a reacted N-isopropylacrylamide, N,N'-diethylacrylamide, 2-carboxyisopropylamide, N-(L)-(1-hydroxymethyl)propylmeth-acrylamide or N-acryloxyl-N'-alkylpiperazine.

The stimulus-responsive polymer may further comprise a hydrophobic pendant group, and the hydrophobic pendant group may in certain embodiments have a structure of formula XII:

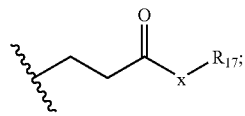

formula XIII:

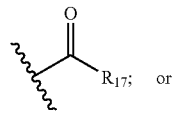

formula XIV:

wherein:
x is O or NH; and
$R_{17}$ is substituted or unsubstituted $C_{3-30}$ alkyl, substituted or unsubstituted $C_{4-30}$ alkenyl, substituted or unsubstituted $C_{4-30}$ alkynyl, substituted or unsubstituted $C_{3-8}$ cycloalkyl, substituted or unsubstituted $C_{6-18}$ aryl, any of which may optionally contain one or more heteroatoms selected from the group consisting of N, O and S.

The hydrophobic pendant group may comprise a reacted 4-tert-butylcyclohexyl acrylate, 2-butoxyethyl acrylate, 2-hexyl acrylate, 2-ethylhexyl acrylate, octadecyl acrylate, lauryl acrylate, diacetone acrylamide, N-(butoxymethyl)acrylamide, N-(isobutoxymethyl)acrylamide, cholesteryl chloroformate, nanonoyl chloride, undecanoyl choride, lauroyl chloride, 4-heptylbenzoyl chloride, myristoyl chloride, 1-bromo-2-cyclohexylethane, 1-bromooctane, 1-adamantyl bromomethyl ketone, 2-bromo-2',5'-dimethyoxyacetophenone, 1-bromo-3,7-dimethyloctane, 1-bromododecane, 1-bromooctane, 1-bromodecane, 1-bromooctadecane, 2-(6-bromohexyloxy)tetrahydro-2H-pyran, 1-iodoadamantane, 1-iodohexane, 1-iodooctane, 1-iododecane, 1-iodododecane or 1-iodooctadecane.

In another aspect, there is provided a composition comprising a stimulus-responsive polymer as defined herein and a cross-linking group.

The polymer may be cross-linked by a cross-linking group having a structure of formula XI:

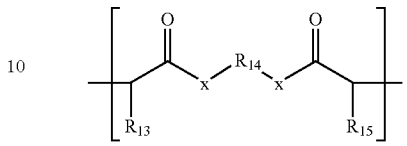

wherein:
x is O or NH;
each of $R_{13}$ and $R_{15}$ is independently hydrogen, hydroxyl, halide, thiohydroxyl or hydrocarbyl; and
$R_{14}$ is unsubstituted or substituted $C_{1-30}$ alkylene optionally containing one or more heteroatoms selected from the group consisting of N, O and S; unsubstituted or substituted $C_{2-30}$ alkenylene optionally containing one or more heteroatoms selected from the group consisting of N, O and S; or unsubstituted or substituted $C_{2-30}$ alkynylene optionally containing one or more heteroatoms selected from the group consisting of N, O and S.

In particular embodiments, the cross-linking group may comprise a cross-linked 1,4-butanediol diacrylate, 1,4-butanediol dimethacrylate, 1,2-ethanediol diacrylate, 1,6-hexanediol diacrylate, 2,5-hexanediol diacrylate, poly(ethyl glycol)diacrylate, ethylene diacrylate, 1,3-propanediol diacrylate, including 1,4-Bis(acryloyl)piperazine, N,N'-Bis(acryloyl)cystamine, N,N'-methylenebisacrylamide, N,N'-(1,2-Dihydroxyethylene)bisacrylamide, 1,3-dibromo-2-propanol, 1,4-dibromo-2-butanol, 1,5-dibromo pentane, 1,6-dibromo hexane, 1,5-diiodo pentane, 1,8-dibromo octane, 1,6-diiodo hexane or 1,8-diiodo octane.

There is also presently provided, in another aspect, a method of preparing a stimulus-responsive polymer as defined herein, the method comprising reacting a biodegradable polymer comprising a poly(amino ester) or poly(amido amine), in order to form a polymer having a stimulus-responsive pendant group attached to the polymer backbone, wherein the poly(amido amine) optionally comprises a disulfide linkage.

In certain embodiments, the biodegradable polymer has at least one secondary amine linkage and at least one tertiary amine linkage in the backbone.

The ratio of units of the biodegradable polymer to the stimulus-responsive molecule may be from about 10:1 to about 1:4.

The method may further comprise cross-linking the biodegradable polymer having a stimulus-responsive pendant group attached to the polymer backbone with a cross-linking molecule. The cross-linking molecule may comprise a diacrylate, a diacrylamide or a dibromo- or diiodo-reagent.

The ratio of units of the biodegradable polymer to the cross-linking molecule may be from about 20:1 to about 1:2.

The method may further comprise reacting the biodegradable polymer having a stimulus-responsive pendant group attached to the polymer backbone with a hydrophobic molecule to attach a hydrophobic pendant group to the polymer backbone.

The ratio of units of the biodegradable polymer to the hydrophobic molecule may be from about 20:1 to about 1:4.

In yet another aspect, there is provided a composition comprising a stimulus-responsive biodegradable polymer as defined herein or a composition as defined herein, and a bioactive agent. The composition may form a micelle or a hydrogel.

The bioactive agent may comprise a small molecule, an organometallic compound, a nucleic acid, a protein, a peptide, a polynucleotide metal, an isotopically labelled chemical compound, a drug, a vaccine, or an immunological agent.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION

Figure 1:
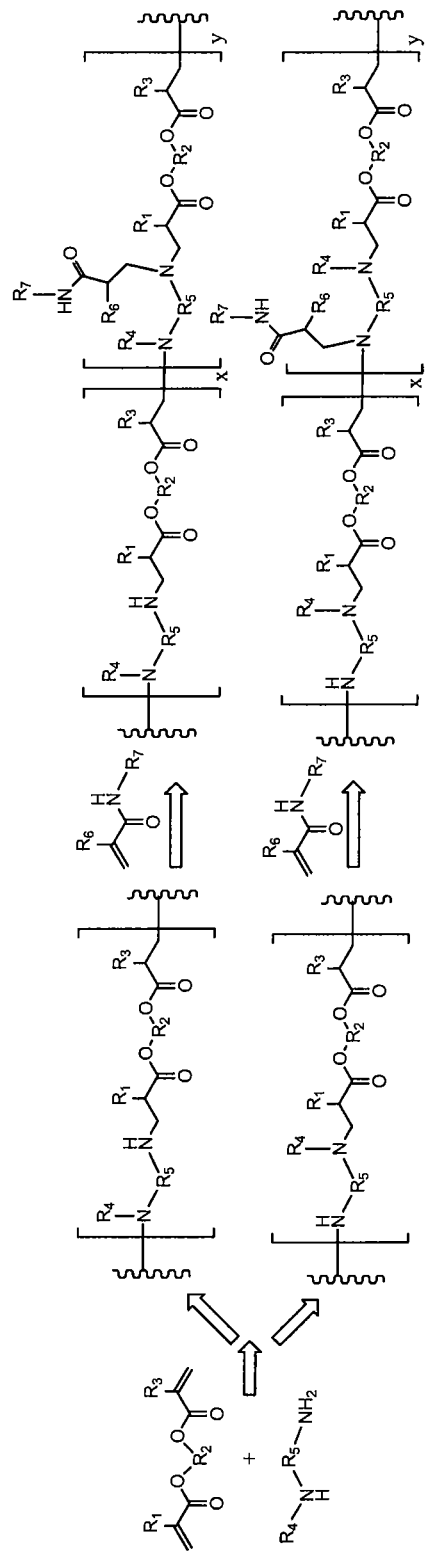
FIG. 1 is a schematic representation of two possible structures of stimulus-responsive polymers of the invention that could form by reacting a diamine monomer with a bis(acrylate ester), followed by grafting of a thermal responsive group.

The present invention relates to stimulus-responsive biodegradable polymers. These polymers comprise a biodegradable polymer backbone having a stimulus-responsive pendant group attached.

The biodegradable polymer backbone comprises a poly (amino ester) or comprises a poly(amido amine), for example a poly(amido amine) that contains a disulfide linkage.

Poly(amino ester)s are good candidate biomaterials for biomedical applications, including for use as vectors for drug and DNA delivery, due to their pH-sensitivity, biodegradablity and biocompatiblity. Poly(amido amine)s containing a disulfide linkage are stable to allow for formulation, manipulation and delivery of the stimulus-responsive polymer, but are biodegradable in the presence of a thiol-containing compound, for example glutathione. As well, poly(amino ester)s, poly(amido amine)s and stimulus-responsive polymers derived from such polymers can easily be prepared using simple and efficient synthesis methods.

Thus, the present polymers are biocompatible and biodegradable, and undergo a chemical or physical change in response to a particular stimulus due to the stimulus-responsive pendant group. The stimulus-responsive polymers can then be formed into various structures, including hydrogels and micelles, by selection of particular cross-linking groups or additional hydrophobic pendant groups.

The term "biodegradable" is intended to mean that a given substance is capable of being broken down or decomposed under natural conditions, including those found within a cell or organism, including by chemical or enzymatic degradation mechanisms.

In one aspect, there is provided a stimulus-responsive polymer comprising a biodegradable polymer backbone and a stimulus-responsive pendant group.

The biodegradable polymer backbone, prior to attachment of the stimulus-responsive pendant group, comprises at least one secondary amine linkage available for attachment of a pendant group through reaction at the nitrogen of the secondary amine. Thus, the polymer backbone, prior to derivitization to become stimulus-responsive, may have at least one secondary amine linkage in the backbone, which secondary amine linkage is available to react with an appropriate pendant group, including a stimulus-responsive pendant group, or a cross-linking group.

The stimulus-responsive polymer may contain at least one amine linkage in the polymer backbone, even after attachment of the stimulus-responsive pendant group and any other pendant groups or cross-linking groups.

The polymer backbone of the stimulus-responsive polymer may be linear or branched, including hyperbranched.

The backbone of the present invention may comprise a poly(amido) amine, including a poly(amido amine) that contains a disulfide linkage, that comprises at least one secondary amine linkage and at least one tertiary amine linkage in the backbone prior to addition of a stimulus-responsive pendant group.

Alternatively, the backbone of the present may comprise a poly(amino ester) comprising at least one secondary amine linkage and at least one tertiary amine linkage in the backbone prior to addition of a stimulus-responsive pendant group.

Suitable poly(amino ester)s and methods for their preparation are described in US 2004/0260115, which is herein incorporated by reference. Thus, in certain embodiments, the backbone comprises a poly(amino ester) compound having a polymer backbone having at least one secondary amine linkage and at least one tertiary amine linkage in the polymer backbone prior to derivitization with a pendant group.

In other embodiments, the poly(amino ester) backbone comprises a poly(amino ester) compound having a polymer backbone having at least one secondary amine linkage and at least one tertiary amine linkage in the polymer backbone and having no terminal primary amino group prior to derivitization with a pendant group.

In particular embodiments, the stimulus-responsive polymer may be a polymer comprising linear units, each independently selected from a linear unit of formula I:

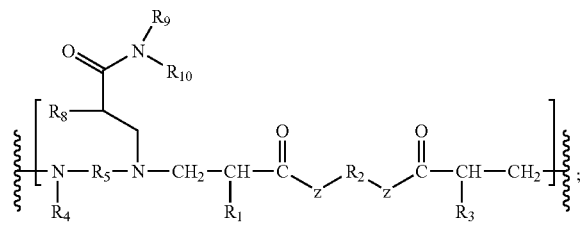

and a linear unit of formula II:

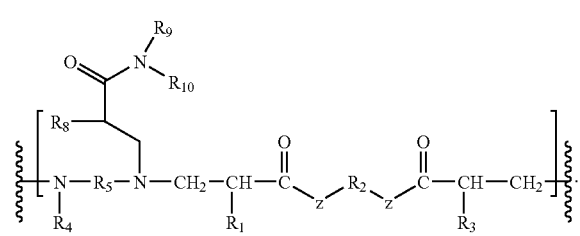

The stimulus-responsive polymer may also optionally comprise one or more units selected from formula III:

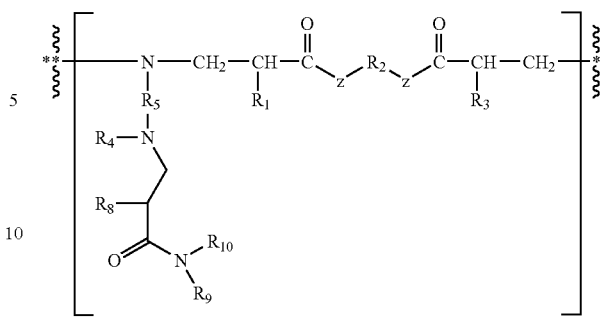

As well, not every structural unit within the polymer will necessarily have an attached stimulus responsive group, and thus the stimulus-responsive polymer may optionally comprise one or more units, each independently selected from formula IV:

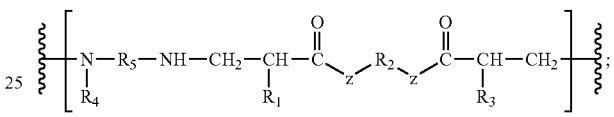

formula V:

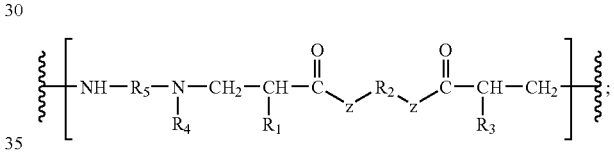

formula VI:

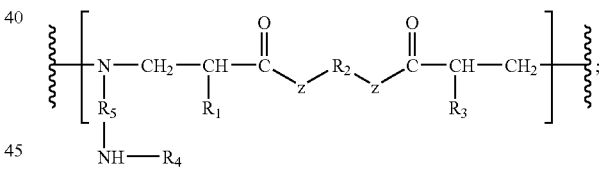

and formula VII:

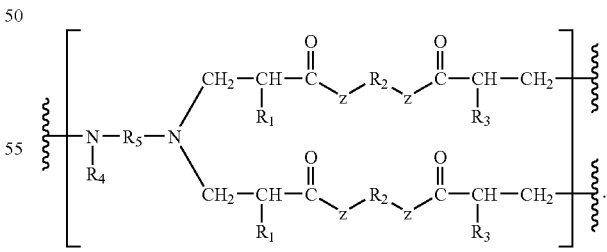

In the above formulae, z is O or NH.

Each of $R_1$, $R_3$ and $R_8$ is independently hydrogen, hydroxyl, halide, thiohydroxyl or hydrocarbyl.

$R_2$ is unsubstituted or substituted $C_{1-30}$ alkylene optionally containing one or more heteroatoms selected from the group consisting of N, O and S; unsubstituted or substituted $C_{2-30}$ alkenylene optionally containing one or more heteroatoms selected from the group consisting of N, O and S; or unsubstituted or substituted $C_{2-30}$ alkynylene optionally containing one or more heteroatoms selected from the group consisting of N, O and S.

$R_5$ is: (i) unsubstituted or substituted $C_{1-30}$ alkylene optionally containing one or more heteroatoms selected from the group consisting of N, O and S; unsubstituted or substituted $C_{2-30}$ alkenylene optionally containing one or more heteroatoms selected from the group consisting of N, O and S; or unsubstituted or substituted $C_{2-30}$ alkynylene optionally containing one or more heteroatoms selected from the group consisting of N, O and S; or (ii) —$R_6$-M-$R_7$—, where $R_6$ is bonded to —N($R_4$)— and is unsubstituted or substituted $C_{1-6}$ alkylene optionally containing one or more heteroatoms selected from the group consisting of N, O and S, or unsubstituted or substituted $C_{2-6}$ alkenylene optionally containing one or more heteroatoms selected from the group consisting of N, O and S; M is CH or N; and $R_7$ is unsubstituted or substituted $C_{1-28}$ alkylene optionally containing one or more heteroatoms selected from the group consisting of N, O and S; unsubstituted or substituted $C_{2-28}$ alkenylene optionally containing one or more heteroatoms selected from the group consisting of N, O and S; or unsubstituted or substituted $C_{2-28}$ alkynylene optionally containing one or more heteroatoms selected from the group consisting of N, O and S.

$R_4$ is (i) hydrocarbyl; or (ii) when $R_5$ is —$R_6$-M-$R_7$—, $R_4$ is also bonded to M and is unsubstituted or substituted $C_{1-6}$ alkylene optionally containing one or more heteroatoms selected from the group consisting of N, O and S, or unsubstituted or substituted $C_{2-6}$ alkenylene optionally containing one or more heteroatoms selected from the group consisting of N, O and S; and $R_4$, M, $R_6$ and the nitrogen atom to which $R_4$ and $R_6$ are bonded form a saturated or unsaturated four- to twelve-membered heterocyclic ring.

$R_9$ is: (i) unsubstituted or substituted $C_{1-30}$ alkylene optionally containing one or more heteroatoms selected from the group consisting of N, O and S; unsubstituted or substituted $C_{2-30}$ alkenylene optionally containing one or more heteroatoms selected from the group consisting of N, O and S; or unsubstituted or substituted $C_{2-30}$ alkynylene optionally containing one or more heteroatoms selected from the group consisting of N, O and S; or (ii) —$R_{11}$-M-$R_{12}$, where $R_{11}$ is bonded to —N($R_{10}$)— and is unsubstituted or substituted $C_{1-6}$ alkylene optionally containing one or more heteroatoms selected from the group consisting of N, O and S, or unsubstituted or substituted $C_{2-6}$ alkenylene optionally containing one or more heteroatoms selected from the group consisting of N, O and S; M is CH or N; and $R_{12}$ is unsubstituted or substituted $C_{1-28}$ alkyl optionally containing one or more heteroatoms selected from the group consisting of N, O and S; unsubstituted or substituted $C_{2-28}$ alkenyl optionally containing one or more heteroatoms selected from the group consisting of N, O and S; or unsubstituted or substituted $C_{2-28}$ alkynyl optionally containing one or more heteroatoms selected from the group consisting of N, O and S.

$R_{10}$ is (i) hydrocarbyl; or (ii) when $R_9$ is —$R_{11}$-M-$R_{12}$, $R_{10}$ is also bonded to M and is unsubstituted or substituted $C_{1-6}$ alkylene optionally containing one or more heteroatoms selected from the group consisting of N, O and S, or unsubstituted or substituted $C_{2-6}$ alkenylene optionally containing one or more heteroatoms selected from the group consisting of N, O and S; and $R_{10}$, M, $R_{11}$ and the nitrogen atom to which $R_9$ and $R_{11}$ are bonded form a saturated or unsaturated four- to twelve-membered heterocyclic ring.

The above formulae have the proviso that $R_1$, $R_2$, $R_3$, $R_4$, $R_5$, $R_8$, $R_9$ and $R_{10}$ cannot have a primary amino group, a secondary amino group, or a C=C double bond conjugated with a carbonyl group.

Thus, in the above described structural formulae, when at least one or more of $R_2$, $R_4$ or $R_5$ contain a disulfide group, particularly when the backbone comprises a poly(amido amine), the polymer backbone will contain a disulfide linkage.

In a particular embodiment of the present invention, the polymer backbone may comprise 1 to 2000 linear units independently selected from a linear unit of formula I and a linear unit of formula II and optionally comprising one or more units of formulae III-VII, as described above.

In certain embodiments, a polymer backbone used to form the stimulus-responsive polymer carries the proviso that when the polymer backbone is a poly(amino ester) and the content of linear units within the polymer backbone is between 20% and 45% and $R_2$ is ethylene, —N($R_4$)—$R_5$—NH— cannot be 1-(2-aminoethyl)piperazinylene, N-ethylethylenedi-aminylene, N-methyl-1,3-propanediaminylene, piperazinylene, or 4-(aminomethyl)piperidinylene, and with the further proviso that when the content of linear units within the polymer backbone is between 20% and 45% and $R_2$ is —(CH$_2$CH$_2$O)$_n$CH$_2$CH$_2$— and n is 5, 7 or 13, —N(R$^4$)—R$^5$—NH— cannot be 1-(2-aminoethyl)piperazinylene, N-ethylethylenediaminyl-ene, N-methyl-1,3-propanediaminylene or 4-(aminomethyl)-piperidinylene.

In the present context, the term "hydrocarbyl" means a hydrocarbon radical that may contain one or more heteroatoms and includes, without limitation, branched and unbranched alkyl, branched and unbranched alkenyl, branched and unbranched alkynyl, aryl, alkoxyl, carbamoyl, carboxyl ester, carbonyldioxyl, amide, alkylthioether, dialkylamino, trialkylamino, cyano, ureido, a substituted alkanoyl group, cyclic, cyclic aromatic, heterocyclic, and aromatic heterocyclic groups, each of which may be substituted with one or more substituents selected from the group consisting of branched and unbranched alkyl, branched and unbranched alkenyl, branched and unbranched alkynyl, dialkylamino, trialkylamino, aryl, ureido, heterocyclic, aromatic heterocyclic, cyclic, aromatic cyclic, halogen, hydroxyl, alkoxy, cyano, amide, carbamoyl, carboxylic acid, ester, carbonyl, carbonyldioxyl, alkylthioether, and thiol groups. Thus, in the present context, the term "hydrocarbyl" includes hydrocarbon radicals that are linked to the compound via a heteroatom, for example, an alkoxy radical.

Thus, suitable values for $R_1$, $R_3$, $R_4$, $R_8$ and $R_{10}$ when these groups are hydrocarbyl include: substituted or unsubstituted $C_{1-30}$ alkyl, substituted or unsubstituted $C_{2-30}$ alkenyl, substituted or unsubstituted $C_{2-30}$ alkynyl, substituted or unsubstituted $C_{3-8}$ cycloalkyl, substituted or unsubstituted $C_{6-18}$ aryl, any of which may optionally contain one or more heteroatoms selected from the group consisting of N, O and S.

In the present context, the term "unit" in the context of the stimulus-responsive polymer refers to a structural unit of the polymer that is covalently bonded to the polymer backbone via one, two or three covalent bonds, and that extends the polymer backbone, and which represents a unit repeated along the polymer, although a unit having a particular structure may be randomly interspersed among units having other particular structures. The term is intended as a generic term covering all possible units in the polymer, including those having the structure of any one of formulae I to VII. It will be appreciated that any given unit may be covalently cross-linked to another unit in the same polymer chain or in a different polymer chain, and such cross-linking attachments are not intended to be included in the above description of backbone covalent attachments between units that extend the polymer backbone.

In the present context, the term "linear unit" refers to a structural unit of the polymer that is covalently bonded to the polymer backbone via two covalent bonds, thereby extending the polymer backbone in a substantially linear manner. A linear unit of the invention may have a structure defined by formulae I-VI.

In the present context, the term "branched unit" refers to a structural unit of the polymer that is covalently bonded to the polymer backbone via three covalent bonds, thereby causing a branching of the polymer backbone. A branched unit of the invention may have a structure defined by formula VII.

In the present context, the term "terminal unit" refers to a structural unit of the poly(amino ester) that occurs at the end or terminus of a polymer chain. The above-described poly (amino ester) may contain two or more terminal units. The terminal unit on the present poly(amino ester)s may have a structure according to the following formula VIII or formula IX:

wherein $R_4$ and $R_5$ are as defined above for formulae I-VII.

FIG. 1 depicts two embodiments of the present stimulus-responsive polymer and types of linkages that may occur in a linear poly(amino ester) prepared by reacting a bis(acrylate) ester and a diamine having a secondary and a primary amino group to form the poly(amino ester) backbone. The structural units are linked in the polymer backbone through one tertiary amine linkage and one secondary amine linkage. Note that in the depicted embodiment the terminal units have an unreacted amino group, either the original secondary amino group, or the original primary amino group.

The polymer backbone may further include end-capping units at the termini of the polymer. Suitable end-capping reagents include morpholine, N-methyl piperazine, N-ethyl piperazine, dimethylamine, diethylamine, and 1-methyl-4-methylamino piperidine, and benzyl-1-piperazine carboxylate.

As referred to herein, the term "stimulus-responsive" or "stimulus-responsiveness" describes or refers to a characteristic of a pendant-group, compound or polymer in which the compound undergoes a change in physical or chemical property in response to an external stimulus, such as a particular pH, temperature, light (including a particular wavelength of light) or ionic strength. For example, the degree of hydrophobicity or hydrophilicity of a compound may change in response to application of the external stimulus, which may result in a change in the solubility of the compound. A particular pendant group, compound or polymer may be responsive to a single stimulus or two or more stimuli, and may exhibit different responses, or changes in physical or chemical characteristic, to different stimuli.

Accordingly, a "stimulus-responsive pendant group" refers to a pendant group that possesses the above-described stimulus responsiveness when grafted onto a polymer backbone, and which provides stimulus-responsiveness to the polymer to which it is grafted.

As stated above, the stimulus may be pH, temperature, light, ionic strength, and the stimulus-responsive pendant group, compound or polymer will undergo a physical or chemical change upon exposure to the particular stimulus.

The stimulus-responsive pendant group may be any stimulus-responsive pendant group. The pendant group may be a stimulus-responsive or an oligomer of stimulus-responsive monomers.

In certain embodiments, the stimulus-responsive pendant group is a temperature-responsive pendant group. In certain embodiments, the stimulus-responsive pendant group comprises caprolactam, ethylene glycol, or propylene oxide.

In other certain embodiments, the stimulus-responsive pendant group comprises an N-substituted acrylamide group.

When the stimulus-responsive pendant group is an N-substituted acrylamide group, the substituent groups on the N-substituted acrylamide group must be less nucleophilic than the secondary amino groups of the polymer backbone, so that the substituent groups do not compete with the secondary amine groups in the backbone for reaction with the vinyl groups in the N-substituted acrylamide.

In certain embodiments, the stimulus-responsive pendant group may have the formula X:

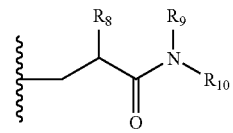

$R_8$, $R_9$ and $R_{10}$ are as defined above for formulae I-VII.

As mentioned above, the stimulus-responsive pendant group may be grafted to the biodegradable polymer backbone via reaction with a secondary amino group in the polymer backbone. However, depending on the particular functional groups present in the polymer backbone and the pendant group prior to grafting, the stimulus-responsive pendant group may be attached via a group other than the secondary amino group in the polymer.

The saturation of available sites in the polymer backbone for grafting of a stimulus-responsive pendant group may be varied by varying the condition of the grafting reaction, as set out below. Accordingly, the stimulus-responsive polymers may contain at least 1%, at least 2%, at least 3%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 97%, at least 98%, at least 99%, or at least 100% grafted stimulus-responsive pendant groups at available sites for grafting. The stimulus-responsive polymers may contain from about 1% to about 99% grafted stimulus-responsive pendant groups or from about 1% to about 100% grafted stimulus-responsive pendant groups.

It will be appreciated that, depending on the particular pendant group used, having too little of the pendant group grafted onto the polymer can result in loss of stimulus-responsiveness. Stimulus-responsiveness and its relationship with graft degree can readily be determined using routine laboratory methods.

Figure 2:
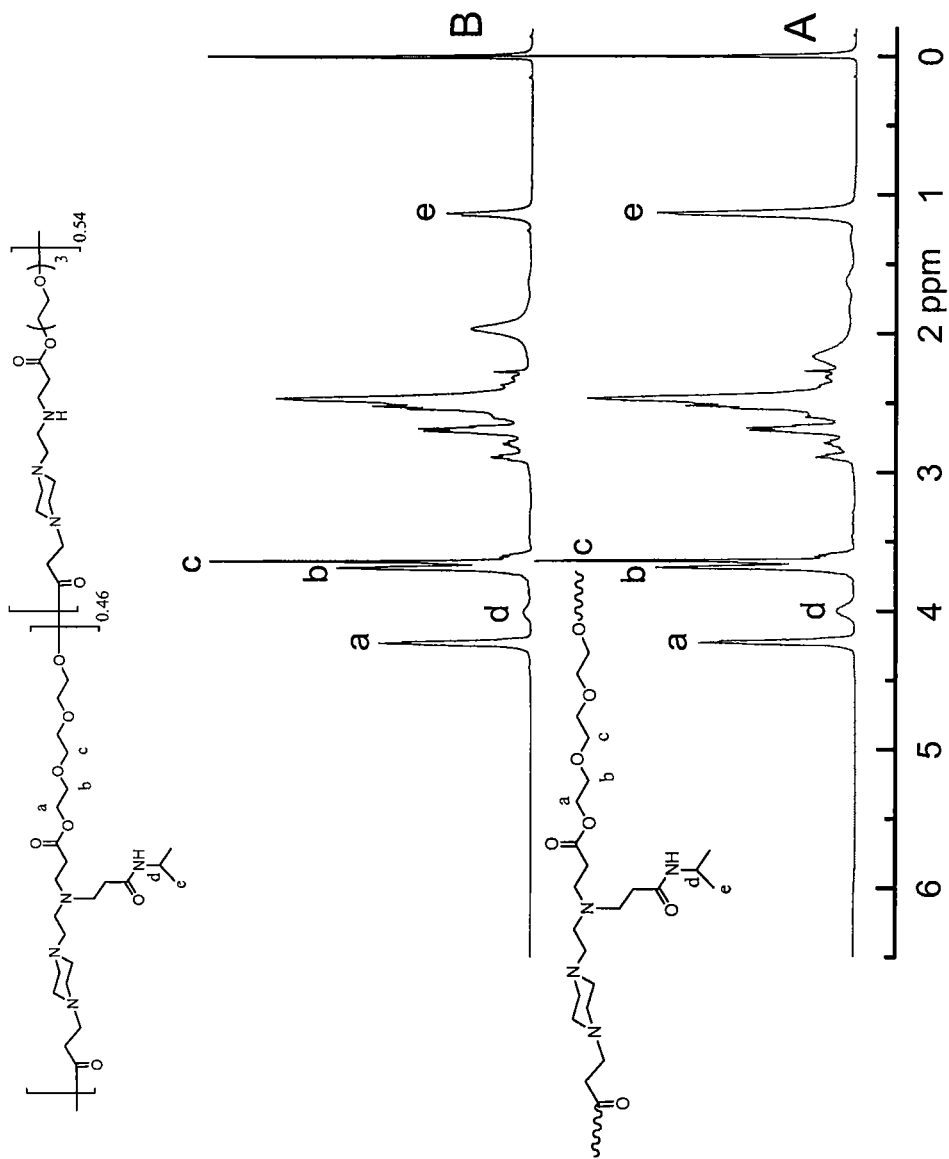
FIG. 2 is an enlarged H-NMR spectrum of poly (PEG258DA-AEPZ)-g-NIPAAm formed by reacting N-aminoethyl piperizine (AEPZ) and poly(ethylene glycol)diacrylate ($M_n$=258)(PEG258DA), followed by reacting linear poly (PEG258DA-AEPZ) with N-isopropylacrylamide: A. 100% graft degree of NIPAAm, and B.46% graft degree of NIPAAm.

FIG. 2 shows that in particular embodiments of the present stimulus-responsive polymer, the $^1$H NMR spectroscopy results for the products of grafting of N-isopropylacrylamide (NIPAAm) onto the poly(amino ester) poly(PEG258DA-AEPZ), and indicates that resulting poly(PEG258DA-AEPZ)-g-NIPAAm was obtained having either 46% or 100% graft degree of NIPAAm.

The hydrophobic or hydrophilic nature of the polymer may be adjusted in order to tune the stimulus-responsiveness of the polymer, so that the stimulus-responsiveness is suitable for a given application. The stimulus-responsiveness may be changed by shifting the ratio of hydrophilic and hydrophobic groups in the polymer. For example, the hydrophilic/hydrophobic property of biodegradable polymer main chain and the nature and graft degree of attached pendant groups, including N-substituted acrylamide pendant groups, may be adjusted to tune the stimulus-responsiveness.

In addition, introducing additional pendant groups that are not temperature-responsive, but that are hydrophilic or hydrophobic may influence the stimulus-responsiveness of the stimulus-responsive polymer.

In embodiments where the stimulus-responsive pendant group is a temperature-responsive group, the polymers will possess a lower critical solution temperature (LCST), defined as the critical temperature at which a polymer solution undergoes phase transition from a soluble to an insoluble state, for example becoming insoluble in aqueous solution above the critical temperature. The LCST can be determined using routine laboratory methods. For example, the LCST may be measured as the transition point in a plot of the transmittance property of an aqueous solution of the stimulus-sensitive polymer as a function of temperature, monitored with a UV spectrometer. Here, the transition point is intended to refer to the point at which the transmittance starts to change from a steady transmittance level (for example at temperatures below the LCST) to an increased or decreased transmittance level, or in reverse, the point at which the transmittance starts to change from an increasing or decreasing transmittance level to a steady transmittance level. See for example FIG. 8.

The LCST of a temperature-responsive polymer may be adjusted so as to be suitable for a given application. For example, the LCST may be chosen so that it falls between room temperature and body temperature for applications where the polymer is to be used within a body. Thus, the polymer may be designed to have one conformation outside of the body and a different conformation within the body.

For example, the poly(PEG258DA-AEPZ)-g-NIPAAm with varying percentages of grafted NIPAAm pendant groups exhibit different LCSTs. As showed in FIG. 6, 100% and 46% graft degree of NIPAAm in the polymer poly(PEG258DA-AEPZ)-g-NIPAAm result in polymers having an LCST of 33 and 36° C., respectively. However, a graft degree of 15% NIPAAm results in the loss of a LCST on the same polymer backbone. For comparison, poly(BDA-AEPZ)-g-NIPAAm having a higher degree of hydrophobicity of the main polymer chain and with a graft degree of 15% NIPAAm still retained an LSCT of 34.5° C. In contrast, poly(PEG575DA-AEPZ)-g-NIPAAm having a higher degree of hydrophilicity of the main polymer chain and with a graft degree of 100% NIPAAm did not demonstrate any LCST.

Protonation of amino groups in the polymer backbone also increases the hydrophilicity of main chain, and thus may be adjusted in order to tune the hydrophilic/hydrophobic balance of the polymer, and thus influencing the stimulus-responsiveness. In addition, the positive charges arising from protonation of the amino groups can prevent, or reduce the extent of, polymer aggregation in which the polymers form large particles when exposure to the relevant stimulus leads to a conformational change in the polymer, for example contraction of the pendant groups.

Figure 7:
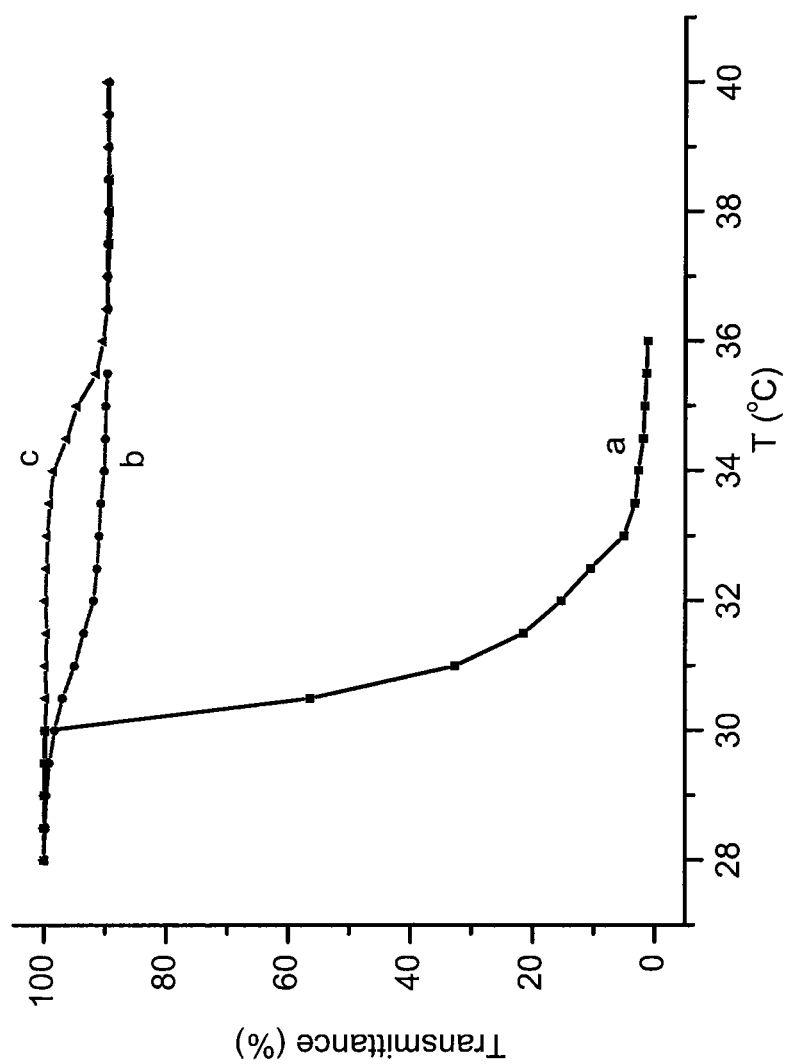
FIG. 7 is the transmittance of 1% (w/v) aqueous solution of poly(BDA-AEPZ)-g-NIPAAm$_{0.6}$ formed by reacting N-aminoethyl piperizine (AEPZ) and 1,4-butanediol diacrylate (BDA), followed by reacting linear poly(BDA-AEPZ) with N-isopropylacrylamide in different pH conditions: a) pH 7, b) pH 5 and c) pH 3.

In a further example, poly(BDA-AEPZ)-g-NIPAAm$_{0.6}$, possesses an LCST of 30.5, 31.0 of 34.5° C. at pH 7, 5 and 3, respectively as shown in FIG. 7. The LCST of the polymer increases as the pH is lowered due to increased hydrophilicity as a result of the partial protonation of the backbone amino groups at pH 5 and complete protonation of the amino groups at pH 3. In addition, reduced aggregation of the polymers is demonstrated by the fact that 89% of transmittance is maintained at 40° C. at pH 5 and 3, compared with only 1% of transmittance at 36° C. at pH 7 as shown in FIG. 7.

The polymer may conveniently be formed into various compositions and structures, including a hydrogel, which is a useful form for stimulus-responsive polymers used in smart drug delivery systems.

A hydrogel is a three-dimensional (3D) network of hydrophilic polymers in which some regions of the network are able to swell in water and hold a large amount of water while other regions of the network are chemically or physically linked each other. The hydrogel is thus able to maintain its structure even when swelled with water. A 3D network can be formed by cross-linking hydrophilic polymers via covalent bonds, hydrogen bonding, van der Waals interactions, or physical entanglement (Kamath et al. *Adv. Drug. Deliv. Rev.*, 1993, 11, 59).

Stimulus-responsive hydrogels prepared using the stimulus-responsive polymer can be used to protect a drug or bioactive agent from hostile environment when administered to a body, for example the presence of enzymes and low pH in the stomach. As well, the hydrogels can be used for site-specific drug release a result of a response by the hydrogel to exposure to an appropriate environmental stimulus.

Stimulus-responsive hydrogels have been developed in a variety of applications, such as in making artificial muscles (Kajiwara et al. *Nature*, 1992, 355, 208; Osada et al. *Nature*, 1992, 355, 242), chemical valves (Osada et al. *Chem. Lett.*, 1985, 9, 1285), immobilization of enzymes and cells (Chen et al. *Biotechnol. Prog.*, 1998, 14, 473), and concentrating dilute solutions in bioseparation (Park et al. *Biotechnol. Prog.*, 1992, 8, 521).

The stimulus-responsive polymer described above can be fashioned into a hydrogel structure by cross-linking of polymer backbones to create a cross-linked polymer network. Thus, the stimulus-responsive polymer may be in the form of a stimulus-responsive hydrogel and includes a cross-linking group connecting two sites in the polymer, including two sites on different polymer chains.

The cross-linking group may be any cross-linking group that connects two sites on one or more polymer chains via a reactive group on one polymer backbone to a reactive group on a second polymer backbone. Each particular reactive group on the polymer backbone that is connected via the cross-linking agent may be the same or different. That is, the cross-linking group, prior to reaction with the polymer backbone, is a bi-functional molecule having two functional groups (typically at either end of the cross-linking molecule) available for reaction with a complementary functional group on the polymer, and the two functional groups on the cross-linking molecule may be the same or different. The cross-linking group may connect via a reactive group on a pendant group, including a stimulus-responsive pendant group, although it will be appreciated that attachment of the cross-linking group to a stimulus-responsive pendant group may influence the stimulus-responsiveness of the resulting hydrogel.

Since the polymer backbone conveniently contains secondary amino functional groups, the cross-linking group may be attached via a secondary amino group on one or more polymer chains. It will be appreciated that if the graft degree of the pendant group on the stimulus-responsive polymer is 100% and the pendant group is attached at the secondary amino groups, then any cross-linking group will be attached via a different functional group on the polymer backbone.

Figure 9:
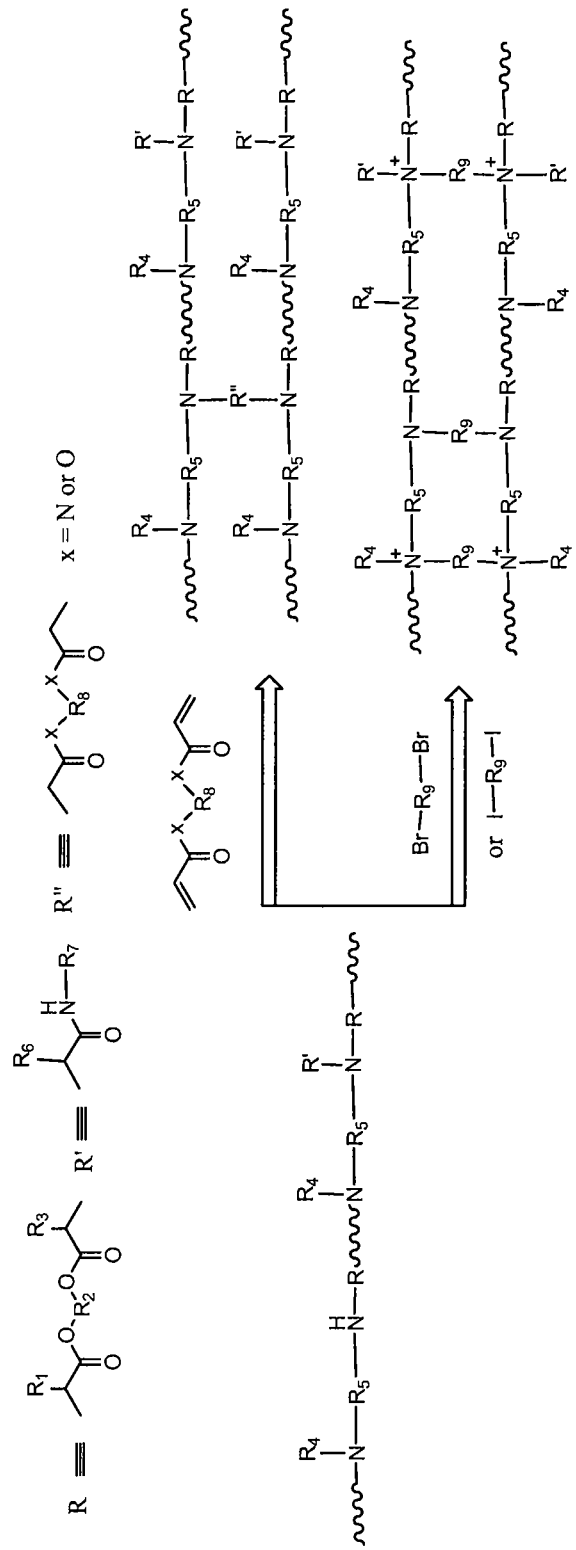
FIG. 9 is a schematic representation of three possible structures of stimulus-responsive biodegradable hydrogels that could form by crosslinking thermal/pH responsive polymers with diacrylates, diacrylamides and dibromo or diiodo reagents.

In certain embodiments, the cross-linking group is attached to two polymer chains via a secondary amino group present in each polymer chain backbone prior to reaction with a cross-linking molecule. In certain embodiments, the cross-linking group is a reacted diacrylate, diacrylamide or dibromo- or diiodo-reagent. FIG. 9 illustrates exemplary hydrogels.

In particular embodiments, the cross-linking group may have the structure of formula XI:

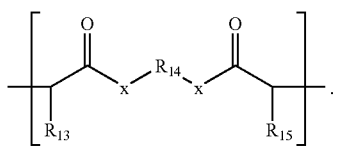

In the above formula XI, x is O or NH.

$R_{13}$ and $R_{15}$ are independently hydrogen, hydroxyl, halide, thiohydroxyl or hydrocarbyl.

$R_{14}$ is unsubstituted or substituted $C_{1-30}$ alkylene optionally containing one or more heteroatoms selected from the group consisting of N, O and S; unsubstituted or substituted $C_{2-30}$ alkenylene optionally containing one or more heteroatoms selected from the group consisting of N, O and S; or unsubstituted or substituted $C_{2-30}$ alkynylene optionally containing one or more heteroatoms selected from the group consisting of N, O and S.

The stimulus-responsive hydrogels may contain at least 1%, at least 2%, at least 3%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 97%, at least 98%, at least 99%, or at least 100% degree of cross-linked contents, as determined by the amount of cross-linking molecule added and the number of sites available for cross-linking. The stimulus-responsive polymers may contain from about 1% to about 99% cross-linking groups or from about 1% to about 100% cross-linking groups.

As well as being suited to being formed into a hydrogel structure, the present stimulus-responsive polymer may be designed as amphiphilic molecules, suitable for formation into a composition of polymeric micelles in aqueous solution.

Polymeric micelles can be formed by aggregation of amphiphilic polymers in aqueous medium due to aggregation of the hydrophobic portions of the polymers to form an inner hydrophobic core that excludes water and an outer hydrophilic surface. Polymeric micelles can encapsulate guest molecules in the hydrophobic core, so they are useful for delivery of bioactive agents.

Amphiphilic stimulus-responsive polymers can be obtained by introducing hydrophobic groups into the inventive stimulus-responsive polymer in the same manner as described above for inclusion of cross-linking groups. That is, a hydrophobic group may be attached to the polymer backbone via a functional group in the polymer backbone, including via an available secondary amino group.

The hydrophobic group may be any hydrophobic group that is hydrophobic in nature and is attached to the polymer backbone via a functional group on the hydrophobic group reacting with a complementary functional group on the polymer backbone. That is, the hydrophobic group, prior to reaction with the polymer backbone, is a mono-functional molecule having a hydrophobic portion and a functional group available for reaction with a complementary functional group on the polymer.

Since the polymer backbone conveniently contains secondary amino functional groups and tertiary amino groups, the hydrophobic group may be attached via a secondary and/or tertiary amino group on the polymer chain, or may be attached at a different functional group on the polymer. It will be appreciated that if the graft degree of the stimulus-responsive pendant group on the stimulus-responsive polymer is 100% and the pendant group is attached at the secondary amino groups, then any hydrophobic pendant group will be attached via a different functional group on the polymer backbone.

Figure 10:
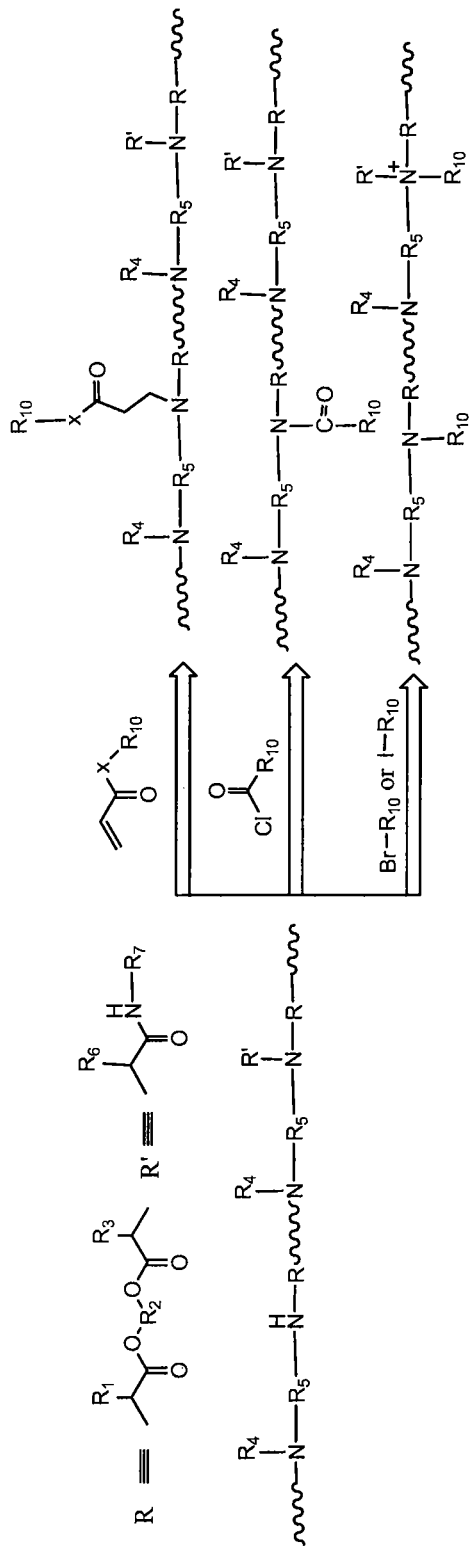
FIG. 10 is a schematic representation of three possible structures of amphiphilic stimulus-responsive polymers that could be formed by introducing hydrophobic groups onto stimulus-responsive polymers through the Michael addition of secondary amines in poly(amino ester) backbone with acrylates and acrylamides, acylation reactions of secondary amines in poly(amino ester) backbone and acyl chlorides, and a alkylation or quaternization reaction of secondary and tertiary amines in poly(amino ester) backbone and monobromo or monoiodo reagents.

In certain embodiments, the hydrophobic group is attached to a polymer backbone via a secondary amino group or tertiary amino group present in the backbone prior to reaction with a hydrophobic pendant group molecule. In certain embodiments, the hydrophobic group is a reacted hydrophobic acrylate, hydrophobic acrylamide, acyl chloride, or monobromo or monoiodo reagent. FIG. 10 illustrates exemplary amphiphilic stimulus-responsive poly(amino esters).

The hydrophobic group may have the structure depicted in formulae XII-XIV below, where x=O for an acrylate and x=NH for an acrylamide in formula XII.

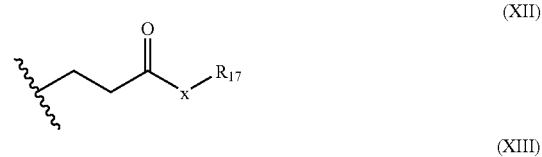

(XII)

(XIII)

(XIV)

In formulae XII-XIV, x is O or NH.

$R_{17}$ is a hydrophobic hydrocarbyl group. $R_{17}$ may be a synthetic hydrophobic group or a naturally occurring hydrophobic group. It will be appreciated that $R_{17}$ should be selected to have low toxicity, that is to be biocompatible.

Thus, suitable values for $R_{17}$ include substituted or unsubstituted $C_{3-30}$ alkyl, substituted or unsubstituted $C_{4-30}$ alkenyl, substituted or unsubstituted $C_{4-30}$ alkynyl, substituted or unsubstituted $C_{3-8}$ cycloalkyl, substituted or unsubstituted $C_{6-18}$ aryl, any of which may optionally contain one or more heteroatoms selected from the group consisting of N, O and S.

The amphiphilic stimulus-responsive polymers of the invention may contain at least 1%, at least 2%, at least 3%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 97%, at least 98%, or at least 99% degree of hydrophobic contents. The stimulus-responsive polymers may contain from about 1% to about 99% grafted hydrophobic pendant groups or from about 1% to about 100% grafted hydrophobic pendant groups, or at least 1%, at least 2%, at least 3%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 97%, at least 98%, or at least 99% grafted hydrophobic pendant groups, as determined by available sites for attachment of the hydrophobic group.

The above-described stimulus-responsive polymers can be readily prepared using standard chemistry methods, including Michael addition reactions. The poly(amino ester) backbone of the present stimulus-responsive polymers may be prepared via the Michael addition of a bis(acrylate ester) monomer to a diamine monomer in the case of poly(amino ester)s or of a bisacrylamide monomer to a diamine monomer in the case of poly(amido amine)s, wherein the diamine monomer has one primary amino group and one secondary amino group. Suitable methods for preparation of the poly(amino ester)s backbone prior to addition of the stimulus-responsive pendant group are described in US 2004/0260115, which is herein incorporated by reference.

If a linear backbone is desired, the bis(acrylate ester) or bisacrylamide and the diamine are reacted in approximately equimolar amounts.

In particular embodiments, the biodegradable polymer backbone may be formed using a bis(acrylate ester) or bisacrylamide monomer of formula XV:

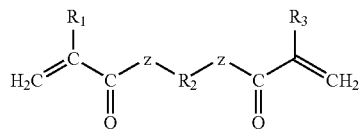

In formula XV, z is O or NH. Each of $R_1$ and $R_3$ is independently hydrogen, hydroxyl, halide, thiohydroxyl or hydrocarbyl; and $R_2$ is unsubstituted or substituted $C_{1-30}$ alkylene optionally containing one or more heteroatoms selected from the group consisting of N, O and S; unsubstituted or substituted $C_{2-30}$ alkenylene optionally containing one or more heteroatoms selected from the group consisting of N, O and S; or unsubstituted or substituted $C_{2-30}$ alkynylene optionally containing one or more heteroatoms selected from the group consisting of N, O and S.

The bis(acrylate ester) or bisacrylamide monomer may be reacted with a diamine monomer of formula XVI:

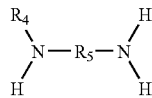

In formula XVI, $R_5$ is:

(i) unsubstituted or substituted $C_{1-30}$ alkylene optionally containing one or more heteroatoms selected from the group consisting of N, O and S; unsubstituted or substituted $C_{2-30}$ alkenylene optionally containing one or more heteroatoms selected from the group consisting of N, O and S; or unsubstituted or substituted $C_{2-30}$ alkynylene optionally containing one or more heteroatoms selected from the group consisting of N, O and S; or (ii) —$R_6$-M-$R_7$—, where $R_6$ is bonded to —N($R_4$)— and is unsubstituted or substituted $C_{1-6}$ alkylene optionally containing one or more heteroatoms selected from the group consisting of N, O and S, or unsubstituted or substituted $C_{2-6}$ alkenylene optionally containing one or more heteroatoms selected from the group consisting of N, O and S; M is CH or N; and $R_7$ is unsubstituted or substituted $C_{1-28}$ alkylene optionally containing one or more heteroatoms selected from the group consisting of N, O and S; unsubstituted or substituted $C_{2-28}$ alkenylene optionally containing one or more heteroatoms selected from the group consisting of N, O and S; or unsubstituted or substituted $C_{2-28}$ alkynylene optionally containing one or more heteroatoms selected from the group consisting of N, O and S.

In formula XVI, $R_4$ is (i) hydrocarbyl; or (ii) when $R_5$ is —$R_6$-M-$R_7$—, $R_4$ is also bonded to M and is unsubstituted or substituted $C_{1-6}$ alkylene optionally containing one or more heteroatoms selected from the group consisting of N, O and S, or unsubstituted or substituted $C_{2-6}$ alkenylene optionally containing one or more heteroatoms selected from the group consisting of N, O and S; and $R_4$, M, $R_6$ and the nitrogen atom to which $R_4$ and $R_6$ are bonded form a saturated or unsaturated four- to twelve-membered heterocyclic ring.

Formulae XV and XVI have the proviso that $R_1$, $R_2$, $R_3$, $R_4$ and $R_5$ cannot have a primary amino group, a secondary amino group, or a C=C double bond conjugated with a carbonyl group. The R groups on the diamine monomer and bis(acrylate ester) or bisacrylamide monomer must be less nucleophilic than the secondary and primary amino groups of the diamine, so that the R groups do not compete with the amino groups for reaction with the vinyl groups in the bis(acrylate ester) or bisacrylamide.

In the present context, the term "diamine monomer" refers to compounds having one secondary amino group and one primary amino group but does not exclude compounds that further comprise one or more tertiary amino groups. Thus, as used herein, the term "diamine monomer" includes compounds having one secondary amino group, one primary amino group and optionally one or more tertiary amino groups.

Bis(acrylate ester) monomers that may be used to prepare poly(amino ester)s of the present invention include 1,4-butanediol diacrylate, 1,4-butanediol dimethacrylate, 1,2-ethanediol diacrylate, 1,6-hexanediol diacrylate, 2,5-hexanediol diacrylate, poly(ethyl glycol)diacrylate, ethylene diacrylate and 1,3-propanediol diacrylate.

Bisacrylamide monomers that may be used to prepare poly(amino amide)s of the present invention include N,N'-bis(acryloyl)cystamine, N,N'-methylene bisacrylamide, N,N'-(1,2-dihydroxyethylene)bisacrylamide, 1,4-bis(acryloyl)piperazine, and N,N'-ethylene bis(acrylamide).

Diamine monomers that may be used to prepare the biodegradable polymer of the present invention include 1-(2-aminoethyl)piperazine, N-methyl ethylenediamine, 4-(aminomethyl)piperidine, 4-amino-piperidine, 3-aminopyrrolidine, N-ethylethylenediamine, N-methyl-1,3-propanediamine, N-isopropylethylenediamine, N-hexylethylenediamine, N-butylethylenediamine, N-(2-hydroxypropyl)ethylenediamine, and N,N-diethyldi-ethylene triamine.

The reaction can be carried out over a wide range of temperatures and pressures, although lower temperatures will result in longer reaction times. For example, the reaction can be carried out at a temperature from about −20° C. to about 100° C., or from about −10° C. to about 90° C., from about 0° C. to about 80° C., from about 10° C. to about 70° C., or from about 20° C. to about 50° C. The reaction can be incubated for a period of time, say in the range of from 10 hours to 10 days, from 18 hours to 7 days, from 24 hours to 96 hours, or from 24 to 72 hours.

Preferably, the reaction is carried out in the presence of a solvent or a mixture of several solvents. Solvents that may be used in the method of the present invention include, but are not limited to: dimethylsulfoxide, dimethylformamide, dimethylacetamide, chloroform, dichloromethane, methyl chloride, tetrahydrofuran, methanol, ethanol, isopropanol, water, hexanes, toluene, benzene, carbon tetrachloride, glyme and diethyl ether.

In some cases, the biodegradable polymer may be reacted with an end-capping reagent. Suitable end-capping reagents include, but are not limited to, morpholine, N-methyl piperazine, N-ethyl piperazine, dimethylamine, diethylamine, and 1-methyl-4-methylamino piperidine, and benzyl-1-piperazine carboxylate.

The biodegradable polymer may be used directly or may be purified prior to further use. Purification can be achieved by known techniques, including precipitation, crystallization, chromatography, drying under vacuum, etc. For example, the biodegradable polymer of the invention can also be purified by precipitation with ether, and then washed with fresh ether and dried under vacuum.

The biodegradable polymer backbone is then reacted with a suitable stimulus-responsive molecule, which is grafted onto the backbone as a stimulus-responsive pendant group, as described above. Thus, the stimulus-responsive pendant group is attached via a functional group on the biodegradable polymer backbone.

In certain embodiments, the stimulus-responsive molecule may be an N-substituted acrylamide.

The stimulus-responsive molecule may have the structure of formula XVII:

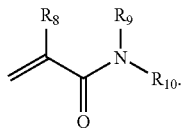

As above, $R_8$ is hydrogen, hydroxyl, halide, thiohydroxyl, carboxyl or hydrocarbyl.

$R_9$ is: (i) unsubstituted or substituted $C_{1-30}$ alkylene optionally containing one or more heteroatoms selected from the group consisting of N, O and S; unsubstituted or substituted $C_{2-30}$ alkenylene optionally containing one or more heteroatoms selected from the group consisting of N, O and S; or unsubstituted or substituted $C_{2-30}$ alkynylene optionally containing one or more heteroatoms selected from the group consisting of N, O and S; or (ii) —$R_{11}$-M-$R_{12}$, where $R_{11}$ is bonded to —N($R_{10}$)— and is unsubstituted or substituted $C_{1-6}$ alkylene optionally containing one or more heteroatoms selected from the group consisting of N, O and S, or unsubstituted or substituted $C_{2-6}$ alkenylene optionally containing one or more heteroatoms selected from the group consisting of N, O and S; M is CH or N; and $R_{12}$ is unsubstituted or substituted $C_{1-28}$ alkyl optionally containing one or more heteroatoms selected from the group consisting of N, O and S; unsubstituted or substituted $C_{2-28}$ alkenyl optionally containing one or more heteroatoms selected from the group consisting of N, O and S; or unsubstituted or substituted $C_{2-28}$ alkynyl optionally containing one or more heteroatoms selected from the group consisting of N, O and S.

$R_{10}$ is (i) hydrocarbyl; or (ii) when $R_9$ is —$R_{11}$-M-$R_{12}$, $R_{10}$ is also bonded to M and is unsubstituted or substituted $C_{1-6}$ alkylene optionally containing one or more heteroatoms selected from the group consisting of N, O and S, or unsubstituted or substituted $C_{2-6}$ alkenylene optionally containing one or more heteroatoms selected from the group consisting of N, O and S; and $R_{10}$, M, $R_{11}$ and the nitrogen atom to which $R_9$ and $R_{11}$ are bonded form a saturated or unsaturated four- to twelve-membered heterocyclic ring.

The above formula XVII has the proviso that $R_8$, $R_9$ and $R_{10}$ cannot have a primary amino group, a secondary amino group, or a C=C double bond conjugated with a carbonyl group.

Conveniently, there are several commercially available N-substituted acrylamide monomers. N-substituted acrylamide monomers that may be used to prepare stimulus-responsive polymers of the present invention include N-isopropylacrylamide, N,N'-diethylacrylamide, 2-carboxyisopropylamide, N-(L)-(1-hydroxymethyl)propylmeth-acrylamide and N-acryloxyl-N'-alkylpiperazine.

The ratio of biodegradable polymer to stimulus-responsive molecule may be from about 10:1 to about 1:4, or from about 5:1 to about 1:2.

The graft reaction is conducted under suitable conditions for reaction between the complementary functional groups that are to be reacted between the stimulus-responsive pendant molecule and the biodegradable polymer.

The graft reaction may be carried out over a wide range of temperatures and pressures, although lower temperatures will result in longer reaction times. For example, the reaction can be carried out between about −20° C. and about 150° C.

Preferably, the graft reaction of the biodegradable polymer is carried out in the presence of a suitable solvent, chosen based on the particular biodegradable polymer and stimulus-responsive pendant group molecule.

For the graft reaction with poly(amino ester)s, the solvents that may be used include dimethylsulfoxide, dimethylformamide, dimethylacetamide, chloroform, dichloromethane, methyl chloride, tetrahydrofuran, toluene, benzene, and carbon tetrachloride.

The graft reaction of the poly(amido amine)s is carried out in the solvents including dimethylsulfoxide, dimethylformamide, dimethylacetamide, tetrahydrofuran, methanol, ethanol, isopropanol, 1-propanol, 1-butanol, and water.

The graft degree of stimulus-responsive pendant group grafted onto the biodegradable polymer can be varied by varying the type of stimulus-responsive molecules used and the relevant amounts thereof present in the reaction. For instance, the presence of an excess of stimulus-responsive monomer tends to increase the graft degree of stimulus-responsive pendant group in the biodegradable polymer. In addition, low steric hindrance of the secondary amino group in the biodegradable polymer, enhancement of reaction temperature, extension of reaction time and selection of suitable solvent may facilitate the graft reaction and increase the graft degree of the stimulus-responsive pendant group in the biodegradable polymer.

As mentioned above, the stimulus-responsive biodegradable polymer may be formed into hydrogels by cross-linking of the stimulus-responsive polymers using cross-linking reagents, including cross-linking molecules such as diacrylates, diacrylamides, di-bromo or di-iodo compounds.

In order to form the hydrogel, the stimulus-responsive biodegradable polymer may be reacted with a suitable cross-linking molecule so that the cross-linking molecule reacts with the poly(amino ester) backbone via functional groups on the backbone, as described above. Thus, the cross-linking group is attached via reaction between complementary functional groups on the cross-linking molecule and the biodegradable polymer backbone.

The cross-linking reaction may be conducted using standard chemistry methods, which methods will depend on the particular functional groups in the cross-linking molecule and in the biodegradable polymer backbone. For example, a diacrylate or diacrylamide may be reacted with a secondary amino group in the polymer backbone by Michael addition. Alternatively, secondary amino groups in the backbone may be alkylated using di-bromo or di-iodo reagents.

Thus, the cross-linking molecule may have a structure of formula XVIII or XIX:

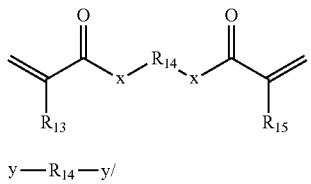

(XVIII)

y—R$_{14}$—y/  (XIX)

x is O or NH.

y is Br or I.

R$_{13}$ and R$_{15}$ are independently hydrogen, hydroxyl, halide, thiohydroxyl or hydrocarbyl.

Conveniently, there are commercially available diacrylates that can be used as a cross-linking molecule to react with the stimulus-responsive polymers, including 1,4-butanediol diacrylate, 1,4-butanediol dimethacrylate, 1,2-ethanediol diacrylate, 1,6-hexanediol diacrylate, 2,5-hexanediol diacrylate, poly(ethyl glycol)diacrylate, ethylene diacrylate and 1,3-propanediol diacrylate.

As well, diacrylamide molecules are commercially available for use as a cross-linking molecule to react with the stimulus-responsive polymers, including 1,4-Bis(acryloyl)piperazine, N,N'-Bis(acryloyl)cystamine, N,N'-methylenebisacrylamide and N,N'-(1,2-Dihydroxyethylene)bisacrylamide.

Dibromo- and diiodo reagents are also commercially available for use as a cross-linking molecule to react with the stimulus-responsive polymers, including 1,3-dibromo-2-propanol, 1,4-dibromo-2-butanol, 1,5-dibromo pentane, 1,6-dibromo hexane, 1,5-diiodo pentane, 1,8-dibromo octane, 1,6-diiodo hexane and 1,8-diiodo octane.

The ratio of stimulus-responsive polymer to cross-linking molecule may be from about 20:1 to about 1:2, or from about 10:1 to about 1:1.

The cross-linking reaction is conducted under suitable conditions for reaction between the complementary functional groups that are to be reacted between the cross-linking molecule and the biodegradable polymer.

The stimulus-responsive biodegradable polymer may also be modified to be amphiphilic, for formation into polymeric micelles. The amphiphilic stimuli-responsive polymers of the present invention may be prepared via introducing hydrophobic groups onto the biodegradable polymer backbones.

The methods for the introduction of hydrophobic groups include the Michael addition of a hydrophobic acrylate or acrylamide to a secondary amine in biodegradable polymer backbone; nucleophilic substitution reactions of a secondary amine in the polymer backbone with acyl chlorides; and alkylation or quaternization reaction of secondary and tertiary amines in biodegradable polymer backbone using monobromo or monoiodo reagents.

The hydrophobic acrylate or acrylamine may have the structure depicted in formula XX below, where x=O for an acrylate and x=NH for an acrylamide; the acyl chloride may have the structure depicted in formula XXI; and the monobromo or monoiodo reagent may have the structure depicted in formula XXII:

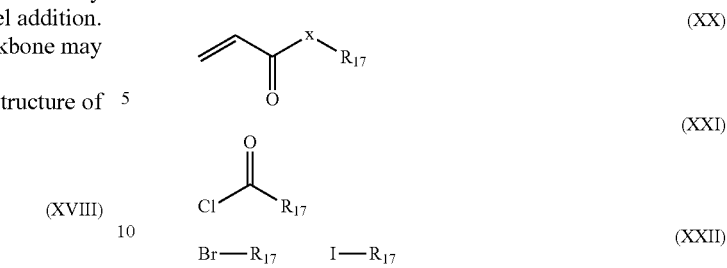

In formulae XX, XXI and XXII, x is O or NH.

R$_{17}$ is a hydrophobic hydrocarbyl group. R$_{17}$ may be a synthetic hydrophobic group or a naturally occurring hydrophobic group. It will be appreciated that R$_{17}$ should be selected to have low toxicity, that is to be biocompatible.

Thus, suitable values for R$_{17}$ include substituted or unsubstituted C$_{3-30}$ alkyl, substituted or unsubstituted C$_{4-30}$ alkenyl, substituted or unsubstituted C$_{4-30}$ alkynyl, substituted or unsubstituted C$_{3-8}$ cycloalkyl, substituted or unsubstituted C$_{6-18}$ aryl, any of which may optionally contain one or more heteroatoms selected from the group consisting of N, O and S.

Conveniently, there are commercially available acrylates that may be used as the hydrophobic pendant group in the present amphiphilic stimulus-responsive poly(amino esters), including 4-tert-butylcyclohexyl acrylate, 2-butoxyethyl acrylate, hexyl acrylate, 2-ethylhexyl acrylate, octadecyl acrylate, and lauryl acrylate.

Commercially available acrylamides that may be used include diacetone acrylamide, N-(butoxymethyl)acrylamide, and N-(isobutoxymethyl)acrylamide.

Commercially available acyl chloride reagents that can be used include cholesteryl chloroformate, nanonoyl chloride, undecanoyl choride, lauroyl chloride, 4-heptylbenzoyl chloride, and myristoyl chloride.

Commercially available monobromo- and monoiodo-reagents that can be used include 1-bromo-2-cyclohexylethane, 1-bromooctane, 1-adamantyl bromomethyl ketone, 2-bromo-2',5'-dimethyoxyacetophenone, 1-bromo-3,7-dimethyloctane, 1-bromododecane, 1-bromooctane, 1-bromodecane, 1-bromooctadecane, 2-(6-bromohexyloxy)tetrahydro-2H-pyran, 1-iodoadamantane, 1-iodohexane, 1-iodooctane, 1-iododecane, 1-iodododecane and 1-iodooctadecane.

The ratio of stimulus-responsive polymer to hydrophobic molecule may be from about 20:1 to about 1:4, or from about 10:1 to about 1:1.

The grafting reaction is conducted under suitable conditions for reaction between the complementary functional groups that are to be reacted between the hydrophobic molecule and the biodegradable polymer.

The stimulus-responsive polymers of the invention may be highly soluble, for example in aqueous solutions. As well, the inventive stimulus-responsive polymers can be readily degraded in aqueous solution due to hydrolysis of the ester linkages, making them very biodegradable. The above described stimulus-responsive polymers may be designed to be biocompatible; the poly(amino ester) or poly(amido amine) main chain has low cytotoxicity and with appropriate selection of the stimulus-responsive pendant group and any cross-linking group or hydrophobic pendant group that may be present, the stimulus-responsive poly(amino ester) or poly(amido amine) may degrade into non-toxic by-products.

Due to the biodegradability and biocompatibility, the biodegradable polymer may be useful as a smart vector for delivering a bioactive agent, such as drug, protein and DNA, to a cell, and smart scaffold for tissue engineering. For example, a hydrogel formed using the stimulus-responsive polymer may be used as a scaffold or support for tissue growth in tissue engineering applications.

In order to deliver a bioactive agent, a stimulus-responsive biodegradable polymer is contacted with the particular agent that is to be delivered to form a complex.

If the bioactive agent is hydrophilic or has a hydrophilic region, it may be associated with charged or hydrophilic regions of the stimulus-responsive polymer through electrostatic or hydrogen-bonding interactions. Bioactive agents, including nucleic acids and proteins, may be covalently attached to the stimulus-responsive polymer for delivery to a cell or organism.

If the bioactive agent is hydrophobic or has a hydrophobic region, it may be encapsulated within the inner core of a polymeric micelle formed using the stimulus-responsive agent. The micelles may be formed by dispersing an amphiphilic stimulus-responsive biodegradable polymer in an aqueous solution along with a bioactive agent that is to be encapsulated. The amphilic polymer will self-assemble to form micelles, and will include a hydrophobic bioactive in the inner core if included in the dispersion.

Since the micelles will be formed from a stimulus-responsive polymer, the micelles can be delivered with the bioactive agent to a subject in an unswelled state, and once delivered to the subject the micelles can be exposed to a stimulus that causes the polymer to swell, thus facilitating release of the bioactive agent at an appropriate site within the body of the subject.

Alternatively, the bioactive agent may be included within a hydrogel formed from a cross-linked stimulus-responsive biodegradable polymer. The bioactive agent may be included in the hydrogel and delivered to the body of a subject. Following delivery, the hydrogel can be exposed to a stimulus that causes release of the bioactive agent from the hydrogel, for example by causing the hydrogel to swell.

The bioactive agents to be delivered using the stimulus-responsive biodegradable polymer may be therapeutic, diagnostic or prophylactic agents. The agent may be, for example, a small molecule, organometallic compounds, nucleic acid, protein, peptide, polynucleotide metal, an isotopically labelled chemical compound, drug, vaccine, immunological agent, etc. The agent may be described as a single entity or compound or a combination of entities or compounds.

In one embodiment, the bioactive agent is a compound with pharmaceutical activity, such as a clinically useful drug. Suitable drugs include but are not limited to: antibiotic, anti-viral agent, anesthetic, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, diuretic, cardiovascular active agent, vasoactive agent, non-steroidal anti-inflammatory agent or nutritional agent.

The bioactive agent to be delivered may also be an agent for use in diagnosis or screening. Diagnostic agents that may be delivered in vivo by the stimulus-responsive poly(amino ester) include gases, metals, commercially available imaging agents used in positron emission tomography (PET), computer assisted tomography (CAT), x-ray, fluoroscopy, and magnetic resonance imaging (MRI), as well as contrast agents. Examples of suitable materials for use as contrast agents in MRI include gadolinium chelates, as well as iron, magnesium, manganese, copper, and chromium or their chelates. Examples of materials useful for CAT and x-ray imaging include iodine-based materials.

Prophylactic agents that may be delivered by the biodegradable polymer of the invention include, but are not limited to, antibiotics, nutritional supplements, and vaccines. Vaccines may comprise isolated proteins or peptides, inactivated organisms and viruses, dead organisms and viruses, genetically altered organisms or viruses, and cell extracts.

In one embodiment, the bioactive agent to be delivered by the stimulus-responsive biodegradable polymer a polynucleotide. A polynucleotide may be any nucleic acid, including but not limited to, RNA and DNA. The polynucleotides may be of any size and sequence, and they may be single- or double-stranded. The polynucleotide may, for example, be greater than 1000 base pairs long or even greater than 10,000 base pairs long. In many cases, the polynucleotide will have been purified prior to use and is substantially free from contaminants, i.e. the polynucleotide is preferably more than about 50% pure, more preferably more than about 75% pure, and most preferably more than about 95% pure. The polynucleotide may be obtained by any means known in the art. Specifically, the polynucleotide may be engineered using recombinant techniques. Alternatively or in addition, the polynucleotide may be obtained from natural sources and purified from contaminating components found normally in nature. Or, the polynucleotide may be chemically synthesized in a laboratory. For example, the polynucleotide is synthesized using standard solid phase chemistry. The polynucleotide may be modified by chemical or biological means, for example to increase stability of the polynucleotide. Methods for modification of polynucleotides include methylation, phosphorylation, end-capping, etc. Derivatives of polynucleotides may also be used in the present invention. These derivatives include modification in the bases, sugars, and/or the phosphate linkage of the polynucleotide.

In one embodiment, a biodegradable polymer agent complex is formed through the contacting of a polynucleotide or salt thereof with a biodegradable polymer of the invention. For this purpose, the biodegradable polymer is preferably at least partially protonated so as to electrostatically interact with the negatively charged polynucleotide. The biodegradable polymer can be protonated, for example, by solubilizing the poly(amino ester) or poly(amido amine) in an aqueous solution of a pH suitable to protonate at least the secondary amines present in the biodegradable polymer. The biodegradable polymer-polynucleotide complex may form nanoparticles that can then be used to deliver the polynucleotides to cells. The biodegradable polymer-polynucleotide complex system can be used to protect the polynucleotide so as to at least partially prevent degradation during the delivery and up-take process. By neutralizing the charge on the backbone of the polynucleotide, the neutral or slightly-positively-charged biodegradable polymer-polynucleotide complex may pass more easily through the hydrophobic membranes of the cell.

In various embodiments, the biodegradable polymer-agent complex of the invention may be used therapeutically in pharmaceutical compositions or medicaments to prevent or treat various diseases. The invention provides corresponding methods of medical treatment, in which a therapeutic dose of a stimulus-responsive biodegradable polymer-bioactive agent complex is administered in a pharmacologically acceptable formulation, e.g. to a patient or subject in need thereof. Accordingly, the invention also provides pharmaceutical compositions comprising a biologically active compound complexed with a stimulus-responsive biodegradable polymer and a pharmacologically acceptable excipient or carrier. The pharmaceutical composition may be soluble in an aqueous solution at a physiologically acceptable pH.

Depending on the intended mode of administration, the pharmaceutical compositions may be in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The composition can include, as noted above, an effective amount of the selected drug in combination with a pharmaceutically acceptable carrier and, in addition, may include other medicinal agents, pharmaceutical agents, carriers, adjuvants, diluents, etc.

The administration in vivo can be performed by parenteral administration, e.g., by intravenous injection including regional perfusion through a blood vessel supplying the tissue(s) or organ(s) having the target cell(s). Other means of administration can include inhalation of an aerosol, subcutaneous, intraperitoneal, or intramuscular injection, direct transfection into, e.g., bone marrow cells prepared for transplantation into an organ that is subsequently transplanted into the subject. Further administration methods can include oral administration, particularly when the complex is encapsulated, or rectal administration, particularly when the complex is in suppository form.

A "therapeutically effective amount" refers to an amount effective, at dosages and for periods of time necessary, to achieve the desired therapeutic result. A therapeutically effective amount of any particular therapeutic agent may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve a desired prophylactic result, such as preventing or inhibiting the rate of various disease onsets or progressions. A prophylactically effective amount can be determined as described above for the therapeutically effective amount. For any particular subject, specific dosage regimens may be adjusted over time according to the individual need and the professional judgement of the person administering or supervising the administration of the compositions.

As used herein a pharmaceutically acceptable carrier or excipient includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such pharmaceutically acceptable carriers and excipients for pharmaceutically active substances is well known in the art. Except insofar as any conventional pharmaceutically acceptable carriers and excipients is incompatible with the active compound, use thereof in the pharmaceutical compositions of the invention is contemplated. Supplementary active compounds can also be incorporated into the compositions.

Pharmaceutical compositions typically must be sterile and stable under the conditions of manufacture and storage. The composition can be formulated as a solution, microemulsion, liposome, freeze-dried powder, spray-dried powder or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, a poly (amino ester)-agent complex can be administered in a time release formulation, for example in a composition which includes a slow release polymer. The active compounds can be prepared with carriers that will protect the compound against rapid release, such as a controlled release formulation, including implants and microencapsulated delivery systems. For this purpose, biodegradable, biocompatible polymers can be used, including but not limited to: ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating the poly(amino ester)- or poly(amido amine)-agent complex in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred met-hods of preparation are vacuum drying, freeze-drying and spray-drying which yields a powder of the active ingredient plus any additional desired ingredient from a previously sterile-filtered solution thereof. In accordance with an alternative aspect of the invention, a biodegradable polymer-agent complex may be formulated with one or more additional compounds that enhance the solubility of the biodegradable polymer-agent complex.

In accordance with another aspect of the invention, pharmaceutical compositions comprising a stimulus-responsive biodegradable polymer-bioactive agent complex may be provided in containers or commercial packages which further comprise instructions for use of the biodegradable polymer-agent complex for therapeutic use such as the prevention and/or treatment of various diseases.

Accordingly, the invention further provides a commercial package comprising a stimulus-responsive biodegradable polymer-bioactive agent complex or the above-mentioned composition together with instructions for the prevention and/or treatment of a relevant disease, and/or packaging or a container.

As used throughout, the term "include" or "including" is intended in a non-limiting sense. Thus, it is intended to indicate inclusion of a particular element or feature without exclusion of any other particular element or feature.

The invention is further exemplified by the following non-limiting examples.

EXAMPLES

Materials and Reagents:

1-(2-aminoethyl)piperazine (AEPZ), poly(ethylene glycol)diacrylate ($M_n$=258) (PEG258DA), N,N'-Bis(acryloyl) cystamine (BAC), N,N'-Methylene bisacrylamide (MBA), N-isopropylacryl-amide (NIPAAm), 1,6-diiodohexane (DIH), and cholesteryl chloroformate (CEC) were purchased from Aldrich (Milwaukee, Wis., USA) and used without further purification.

All other materials, including solvents, were used as received, i.e. without further purification.

General Characterization:

The $^1$H-NMR study was performed on a Bruker DRX-400 spectrometer with $CDCl_3$ and $D_2O$ as solvent. Gel permeation chromatography (GPC) was implemented on a Waters 2690 apparatus with two columns in series (Waters ULTRAHYDROGEL™ 250, 200) and a Waters 410 refractive index detector using 0.5 M acetic acid/0.5 M sodium acetate as the eluent at a flow rate of 0.5 ml/min against poly(ethylene oxide) standards. UV-vis spectra were obtained on a Shimadzu 2501PC spectrometer at room temperature. The reference samples were pure deionized water or 1×PBS buffer. Fluorescence measurement was carried out on a Perkin-Elmer LS 50B photoluminescence spectrometer with a xenon lamp as a light source.

Example 1

Synthesis and Characterization of Linear Poly(Amino Ester)poly(PEG258DA-AEPZ)

AEPZ (11.6 mmol) was dissolved in 25 mL of dimethylsulfoxide (DMSO) at room temperature. PEG258DA (11.6 mmol) was added dropwise to the solution while stirring, followed by rinsing with 5 mL of DMSO. The mixture was stirred at room temperature for about 48 hours. 0.2 g of N-methyl piperazine (NMP) was added and kept stirring for 2 hours to seal end vinyl groups. The product was precipitated from the reaction using 200 mL of diethyl ether under vigorously stirring. The polymer was collected and purified by reprecipitation from a chloroform solution into diethyl ether followed by being dried under vacuum at 50° C. for 24 hours.

A water-soluble poly(amino ester) was obtained having an average molecular weight of 9900 g/mol with a wide molecular weight distribution index of 4.71 as determined by GPC.

Example 2

Synthesis and Characterization of Stimulus-Responsive Polymer Poly(PEG258DA-AEPZ)-g-NIPAAm In a 100 mL of round-bottomed flask, NIPAAm (23.2 or 17.4 mmol) was added into the solution of poly(PEG258DA-AEPZ) (11.6 mmol) in 30 mL of DMSO. The reaction was performed at 80° C. under argon protection for one week. After that, the solution was precipitated into 500 mL of diethyl ether, and the polymer was collected and purified by reprecipitation from a chloroform solution (10 mL) into mixture solutions containing 80 mL of hexane and 20 mL of toluene at 50° C., followed by being dried under vacuum at 50° C. for 24 hours.

The reaction could yield different graft degree of NIPAAm. As shown in FIG. 2, $^1$H NMR spectroscopy was performed to determine the graft degree from the ratio of integrated characteristic relative peaks. As seen in FIG. 2, there are two types of hydrogen ascribed to isopropyl group of NIPAAm, with peaks located at 4.0 ppm (1H, $CH(CH_3)_2$) and 1.1 ppm (6H, $CH(CH_3)_2$), respectively, and one ester characteristic peak of poly(amino ester) as reflected by the peak at 4.2 ppm (4H, $COOCH_2CH_2$—).

Thus, the graft degree of NIPAAm can be determined by Equation 1:

$$GD_{NIPAA}=2I_{1.1}/3I_{4.2}*100\% \text{ or } 4I_{4.0}/I_{4.2}*100\% \qquad \text{Eq. 1}$$

As indicated in FIGS. 2A and 2B, the graft degree of NIPAAm was approximately 100% and 46% after reacting NIPAAm and poly(PEG258DA-AEPZ) at 80° C. for one week with molar ratio 2:1 and 1.5:1 of NIPAAm to poly (PEG258DA-AEPZ), respectively.

Figure 3:
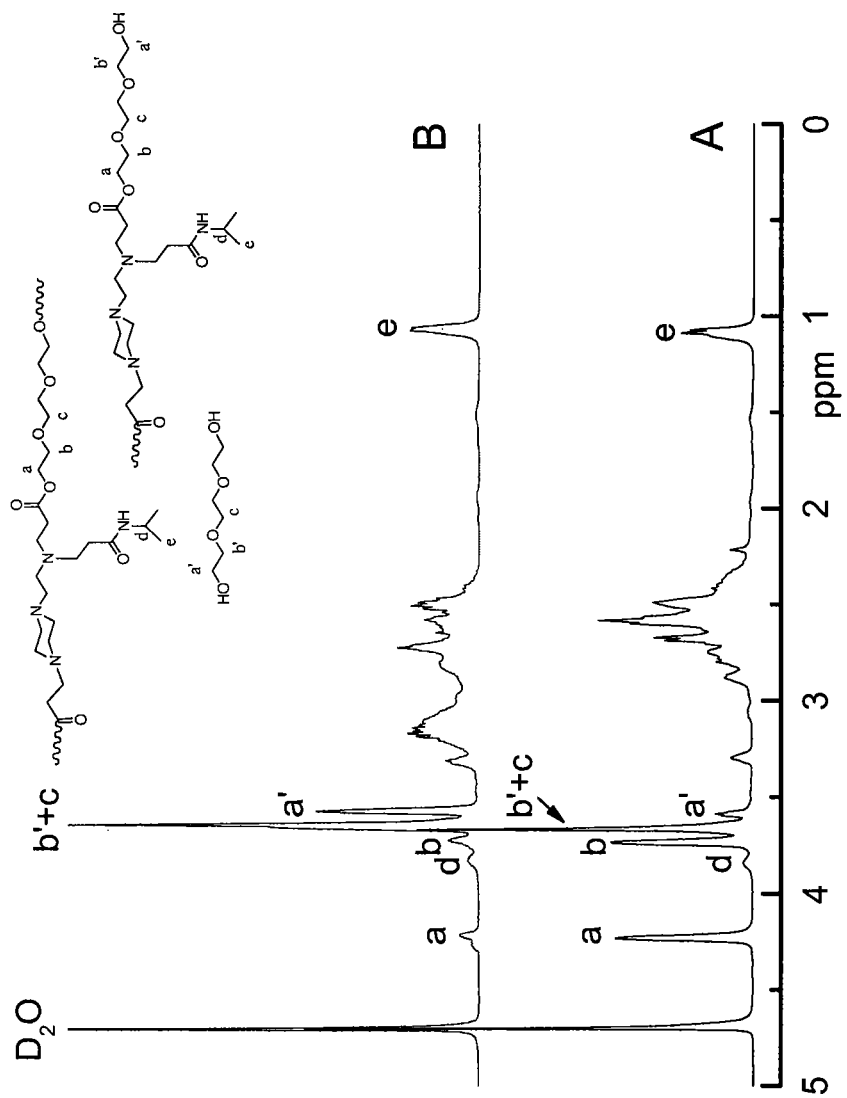
FIG. 3 shows the $^1$H-NMR spectrum of poly(PEG258DA-AEPZ)-g-NIPAAm$_{0.46}$ after being kept in water for A. 2 hours and B. 70 hours.
Figure 4:
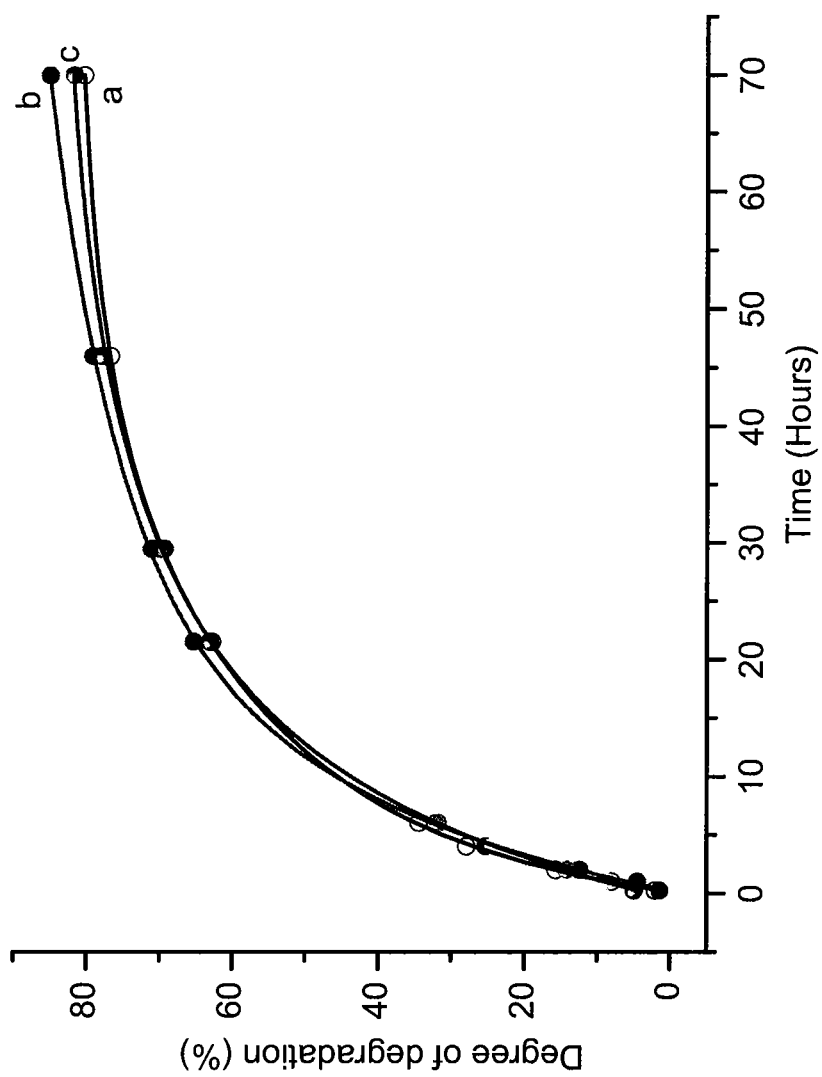
FIG. 4 is the hydrolysis profile of polymer in water: a) poly(PEG258DA-APEZ), b) poly(PEG258DA-AEPZ)-g-NIPAAm$_{0.46}$ and c) poly(PEG258DA-AEPZ)-g-NIPAAm$_{1.0}$.

The poly(PEG258DA-AEPZ)-g-NIPAAm obtained from was tested for degradability. FIG. 3 depicts $^1$H NMR spectra for poly(PEG258DA-AEPZ)-g-NIPAAm$_{0.46}$ in aqueous solution. Upon hydrolysis of the ester group, the peak attributed to the proton attached to the a carbon adjacent to ester group from around 4.2 ppm to 3.6 ppm. Therefore, the degree of hydrolysis degree could be monitored by the change in the ratio of the integrate intensities of the two peaks, $I_{3.6}/(I_{3.6}+I_{4.2})$. As compared, linear poly(PEG258DA-AEPZ) and poly (PEG258DA-AEPZ)-g-NIPAAm$_{1.0}$ were also test for degradability, and the hydrolysis profiles of all three polymers are illustrated in FIG. 4. All the polymers have similar hydrolysis profile independent with the graft degree of NIPAAm, which may be due to similar hydrophilicity of NIPAAm and poly(PEG258DA-AEPZ).

Example 3

Synthesis and Characterization of Stimulus-Responsive Stimulus-Degradable Polymer Poly(BAC/MBA-AEPZ)-g-NIPAAm First, linear poly(BAC/MBA-AEPZ) containing secondary amines in the backbone was prepared. N,N'-Bis(acryloyl) cystamine (BAC, 1.915 mmol) and N,N'-methylene bisacrylamide (MBA, 1.915 mmol) were dissolved in a mixture solvent of 8 mL of methanol and 2 mL of pure water at room temperature. AEPZ (3.83 mmol) was added dropwise to the solution while stirring, followed by rinsing with 2 mL of methanol. The mixture was stirred at 50° C. for about 48 hours. 0.1 g of N-methyl piperazine (NMP) was added and kept stirring for 2 hours to seal end vinyl groups. The product was precipitated from the reaction using 100 mL of cool acetone under vigorously stirring. The polymer was collected and purified by reprecipitation from a methanol solution into cool acetone followed by being dried under vacuum at 50° C. for 24 hours.

In a 25 mL of round-bottomed flask, NIPAAm (7.66 mmol) was added into the solution of poly(BAC/MBA-AEPZ) (3.83 mmol) in a mixture solvent of 10 mL of methanol and 2 mL of pure water. The reaction was performed at 50° C. under argon protection for 6 days. After that, the solution was precipitated into 100 mL of cool acetone, and the polymer was collected and purified by reprecipitation from a methanol solution (10 mL) into cool acetone, followed by being dried under vacuum at 50° C. for 24 hours.

Figure 5:
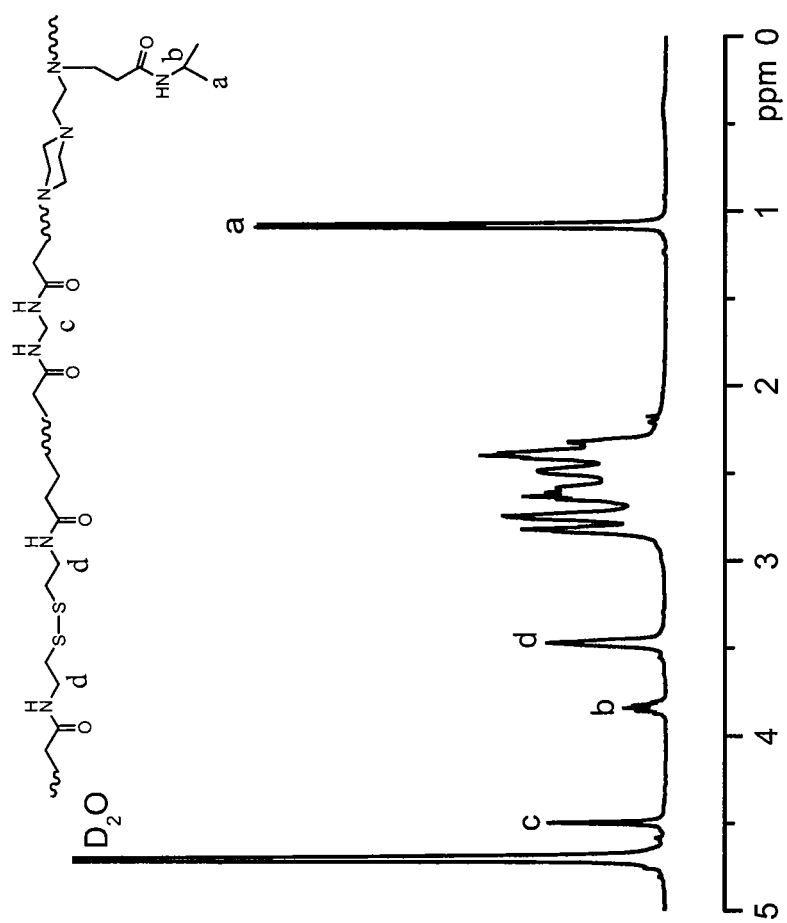
FIG. 5 is an enlarged $^1$H-NMR spectrum of poly(BAC$_{0.5}$/MBA$_{0.5}$-AEPZ)-g-NIPAAm with 70% NIPAAm grafting degree formed by reacting N-aminoethyl piperizine (AEPZ) and a mixture of N,N'-Bis(acryloyl) cystamine (BAC) and N,N'-methylene bisacrylamide (MBA) with a molar ratio rate of AEPZ:BAC:MBA to be 2:1:1, followed by reacting linear poly(BAC/MBA-AEPZ) with N-isopropylacrylamide.

The reaction could yield different graft degree of NIPAAm. As shown in FIG. 5, $^1$H NMR spectroscopy was performed to determine the graft degree from the ratio of integrated characteristic relative peaks. As seen in FIG. 5, there are two types of hydrogen ascribed to isopropyl group of NIPAAm, with peaks located at 3.8 ppm (1H, $CH(CH_3)_2$) and 1.1 ppm (6H, $CH(CH_3)_2$), respectively, and two amide characteristic peaks of MBA and BAC repeat units as reflected by the peak at 4.4 ppm (2H, CONHCH$_2$NHCO) and 3.4 ppm (4H, CONHCH$_2$CH$_2$S—).

Thus, the graft degree of NIPAAm can be determined by Equation 2 if the molar ratio of BAC to MBA is n to m:

$$GD_{NIPAAm}=(n/(n+m))*(2*I_{1.1})/(3*I_{3.4}) \qquad \text{Eq. 2}$$

As indicated in FIG. 5, the graft degree of NIPAAm was approximately 70% after reacting double molars NIPAAm and poly(BAC/MBA-AEPZ) at 50° C. for 6 days.

Example 4

LCST Analysis of Stimulus-Responsive Polymers

Solutions of poly(PEG258DA-AEPZ)-g-NIPAAm, poly(BDA-AEPZ)-g-NIPAAm and poly(BAC/MBA-AEPZ)-g-NIPAAm (1 w/v %) were prepared in 1×PBS buffer (pH=7.4), 0.1 M of NaAC/HAC buffer (pH 5) and citric acid/sodium hydroxide solution/sodium chloride buffer (pH 3). The transmittance of visible light (λ=500 nm) was recorded as a function of solution temperature from 25 to 45° C. At the start of each experiment, the spectrophotometer was calibrated with pure PBS buffer solution. Once a plot of transmittance vs. temperature was obtained, the LCST was judged to be the initial break point of the curve.

Figure 6:
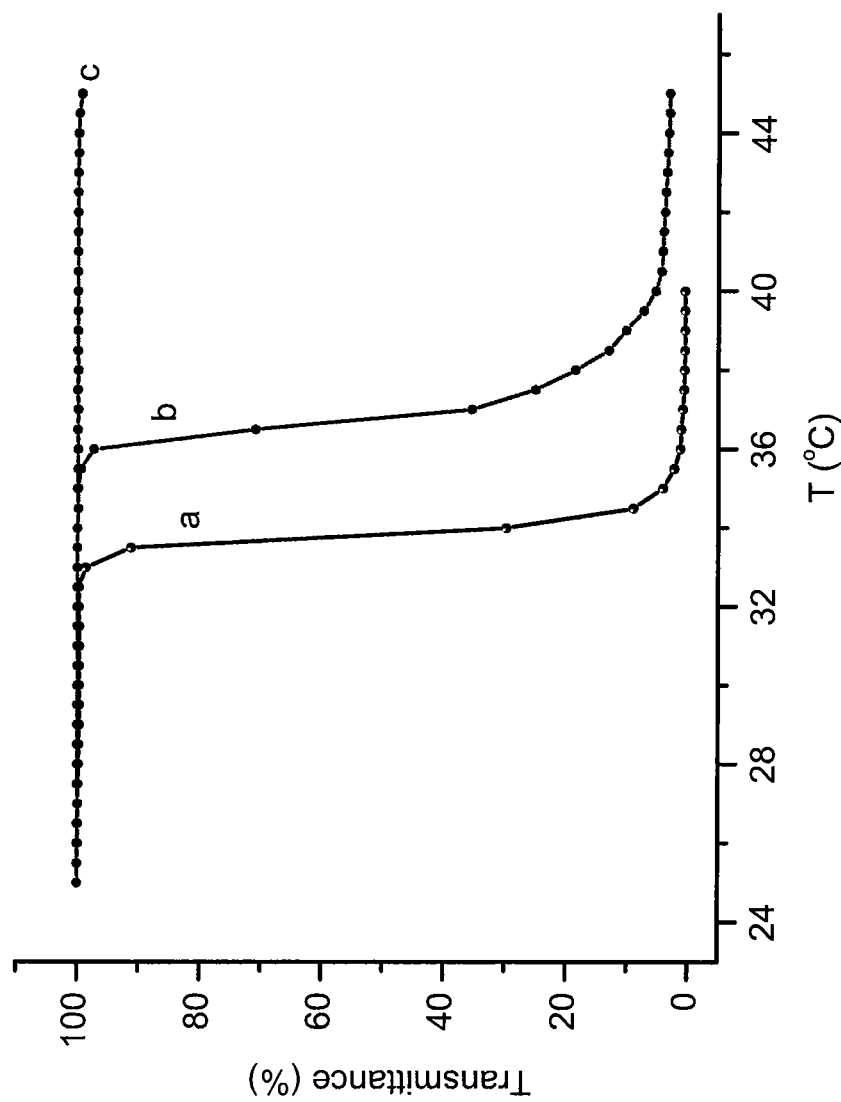
FIG. 6 is the transmittance of 1% (w/v) aqueous solution of poly(PEG258DA-AEPZ)-g-NIPAAm: graft degree of NIPAAm a) 15%, b) 46% and c) 100%.
Figure 8:
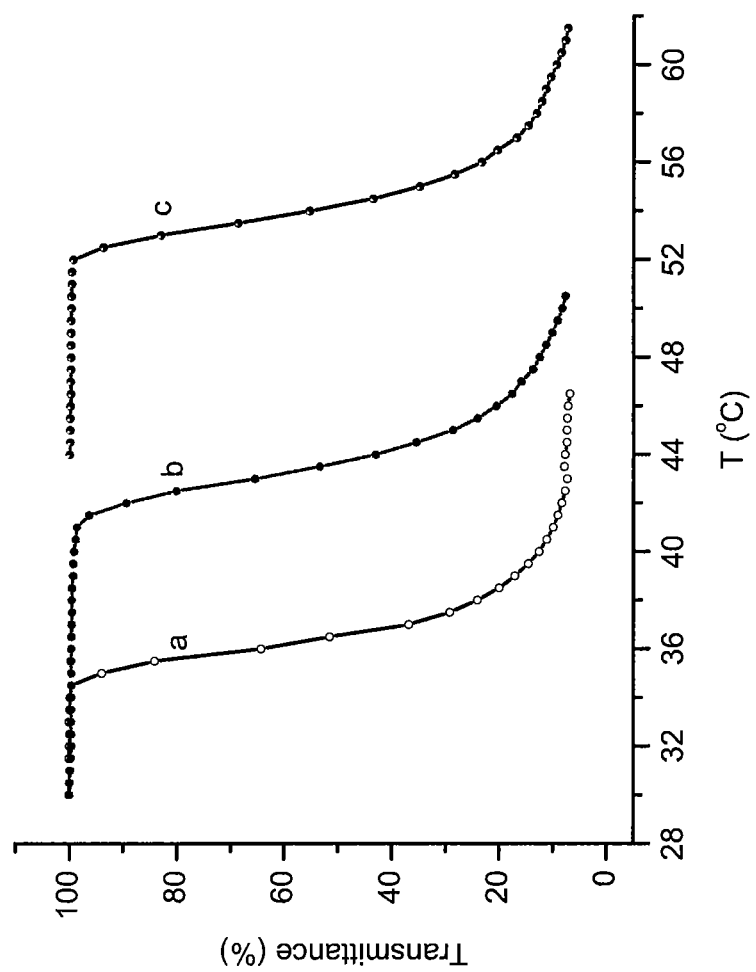
FIG. 8 is the transmittance of 1% (w/v) aqueous solution of a) poly(BAC$_{0.5}$/MBA$_{0.5}$-AEPZ)-g-NIPAAm$_{0.7}$; b) poly (BAC$_{0.4}$/MBA$_{0.6}$-AEPZ)-g-NIPAAm$_{0.76}$; and c) poly (BAC$_{0.33}$/MBA$_{0.67}$-AEPZ)-g-NIPAAm$_{0.8}$.

As shown in FIG. 6, 100% and 46% graft degree of NIPAAm make poly(PEG258DA-AEPZ)-g-NIPAAm having a LCST at 33 and 36° C., respectively, however, 15% graft degree of NIPAAm results in the loss of a LCST. As reflected in FIG. 7, poly(BDA-AEPZ)-g-NIPAAm$_{0.6}$ has a LCST of 30.5, 31.0 and 34.5° C. at pH 7, 5 and 3, respectively. As indicated in FIG. 8, poly(BAC$_{0.5}$/MBA$_{0.5}$-AEPZ)-g-NIPAAm$_{0.7}$, poly(BAC$_{0.4}$/MBA$_{0.6}$-AEPZ)-g-NIPAAm$_{0.76}$, and poly(BAC$_{0.33}$/MBA$_{0.67}$-AEPZ)-g-NIPAAm$_{0.8}$ have LCST of 34.5, 42.0 and 52.5° C. at pH 7, respectively.

Example 5

Preparation of Stimulus-Responsive Hydrogel 0.17 g of 1,6-diiodohexane (DIH) was added into 0.5 g of poly(PEG258DA-AEPZ)-g-NIPAAm$_{1.0}$ in 10 mL of toluene. The mixture was refluxed under argon protection. After two days, the crosslinking hydrogel poly(PEG258-AEPZ)-g-NIPAAm-c-DIH was obtained. The hydrogel was washed by toluene for 3 times to remove residue DIH and dried under vacuum at 50° C. for 24 hours.

Example 6

Synthesis of Amphiphilic Stimulus-Responsive Polymer 0.5 g of poly(PEG258DA-AEPZ)-g-NIPAAm$_{0.46}$ was dissolved in 10 mL of anhydrous CHCl$_3$. 0.5 g of cholesteryl chloroformate (CEC) and 0.18 mL of triethylenamine (TEA) were added in the solution and stirred at room temperature for 2 days under argon. After the reaction, the solution was purified by precipitating into 100 mL of diethyl ether under vigorously stirring. The polymer was collected and purified by reprecipitation from a chloroform solution into diethyl ether followed by being dried under vacuum at 50° C.

Figure 11:
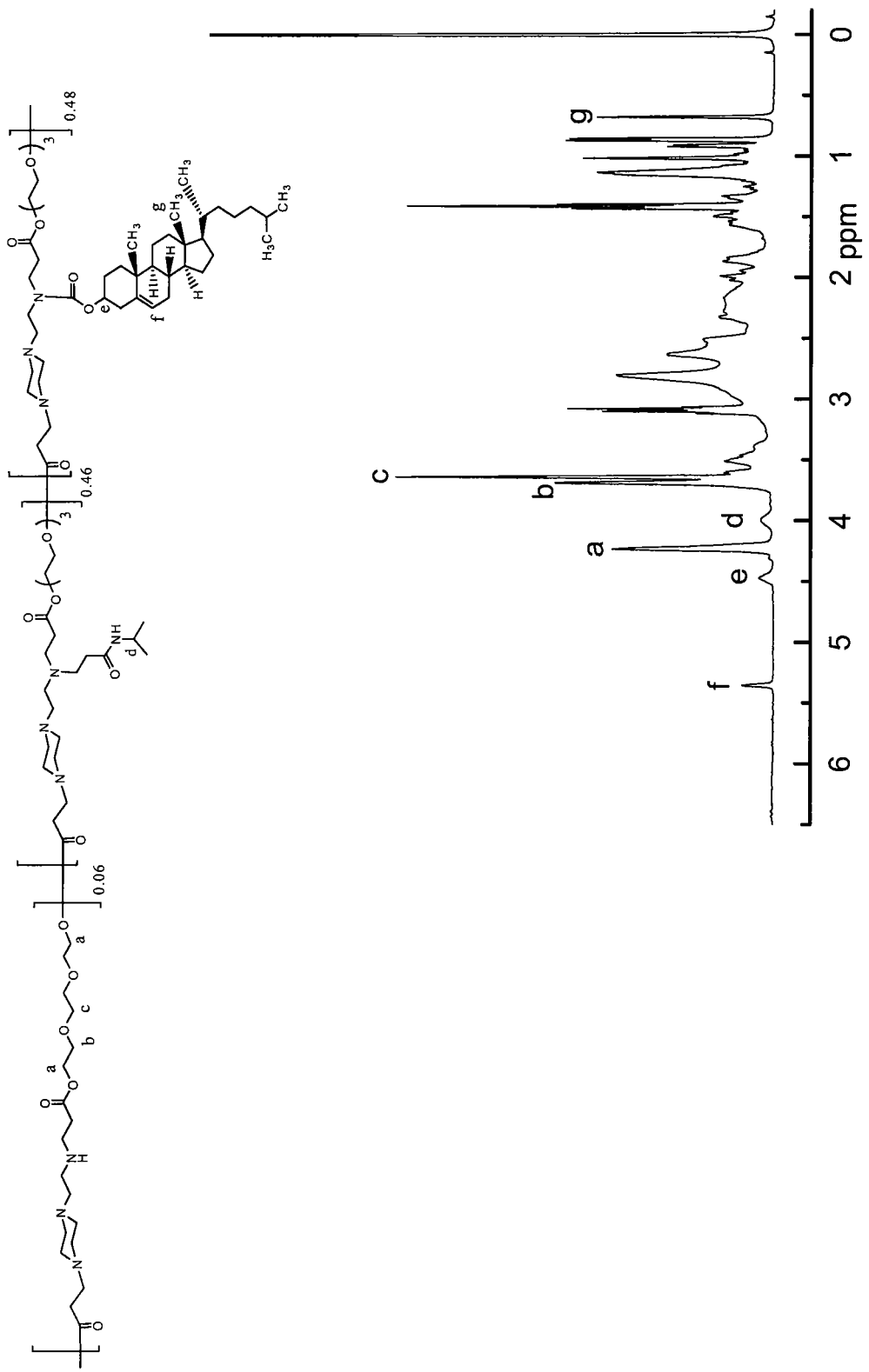
FIG. 11 is an enlarged $^1$H-NMR spectrum of poly (PEG258-AEPZ)-g-NIPAAm$_{0.46}$-CEC$_{0.48}$ formed by acylation reaction of secondary amines with cholesteryl chloroformate.

FIG. 11 is $^1$H NMR spectroscopy of poly(PEG258DA-AEPZ)-g-NIPAAm-CEC and illustrates characteristic peaks of CEC at 0.6 ppm (signal g), 4.5 ppm (signal e) and 5.4 ppm (signal f). The graft degree of CEC in poly(PEG258DA-AEPZ)-g-NIPAAm-CEC was determined from the ratio of integrated characteristic relative peaks as shown in Equation 3:

$$GD_{CEC}=4I_{5.4}/I_{4.2}*100\% \qquad \text{Eq. 3}$$

Therefore, the graft degree of CEC was calculated at 48% based on FIG. 11.

Example 7

Determination of Critical Micelle Concentration (CMC) of poly(PEG258DA-AEPZ)-g-NIPAAm$_{0.46}$-CEC$_{0.48}$ Aliquots of pyrene solution (10 μg/mL in acetone) were added to 4 mL of screw vials, and the acetone was allowed to evaporate. 4 mL of aqueous poly(PEG258DA-AEPZ)-g-NIPAAm$_{0.46}$-CEC$_{0.48}$ solutions of 0.1-200 mg/L were then added to the vials containing the pyrene residues, so that the solution all contained excess pyrene at a concentration of 0.1 μg/mL. The solutions were allowed to equilibrate overnight at room temperature before fluorescence spectra were obtained using a LS50B luminescence spectrometer (Perkin Elmer, U.S.A.).

Figure 12:
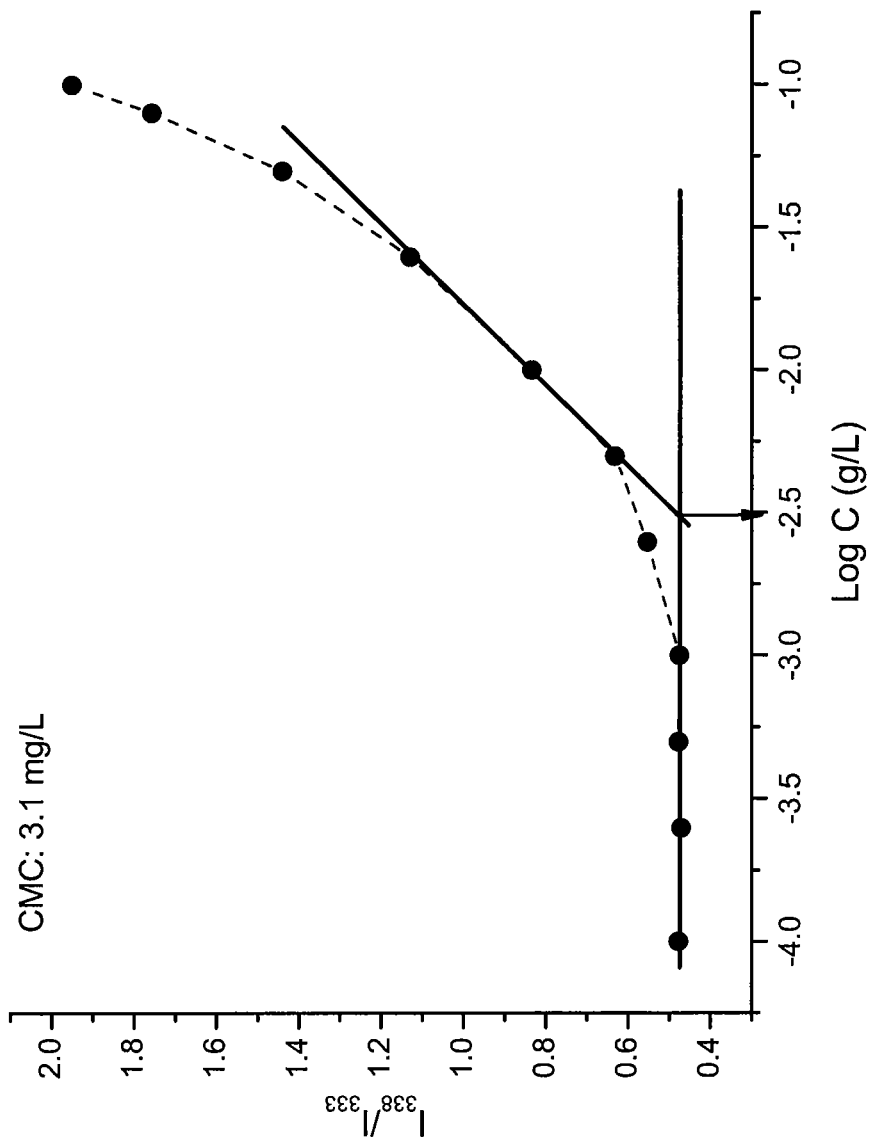
FIG. 12 is a plot of I338/I333 from pyrene excitation spectra as a function of poly(PEG258DA-AEPZ)-g-NIPAAm$_{0.46}$-CEC$_{0.48}$ concentrations.

The excitation spectra (300-360 nm) were recorded with an emission wavelength of 395 nm; the excitation and emission bandwidths were set at 3 nm. The ratios of the peak intensities at 338 nm and 333 nm ($I_{338}/I_{333}$) of the excitation spectra were analyzed as a function of polymer concentration. Its CMC value was taken at 3.1 mg/L from the intersection of the tangent to the curve at the inflection with the horizontal tangent through the points at the low concentrations as shown in FIG. 12.

Example 8

LCST Analysis of Poly(PEG258DA-AEPZ)-g-NIPAAm$_{0.46}$-CEC$_{0.48}$

Solutions of poly(PEG258DA-AEPZ)-g-NIPAAm$_{0.46}$-CEC$_{0.48}$ (1 w/v %) were prepared in 1×PBS buffer, pH=7.4. The transmittance of visible light (λ=500 nm) was recorded as a function of solution temperature from 30 to 45° C. At the start of each experiment, the spectrophotometer was calibrated with pure PBS buffer solution. Once a plot of transmittance vs. temperature was obtained, the LCST was judged to be the initial break point of the curve.

Figure 13:
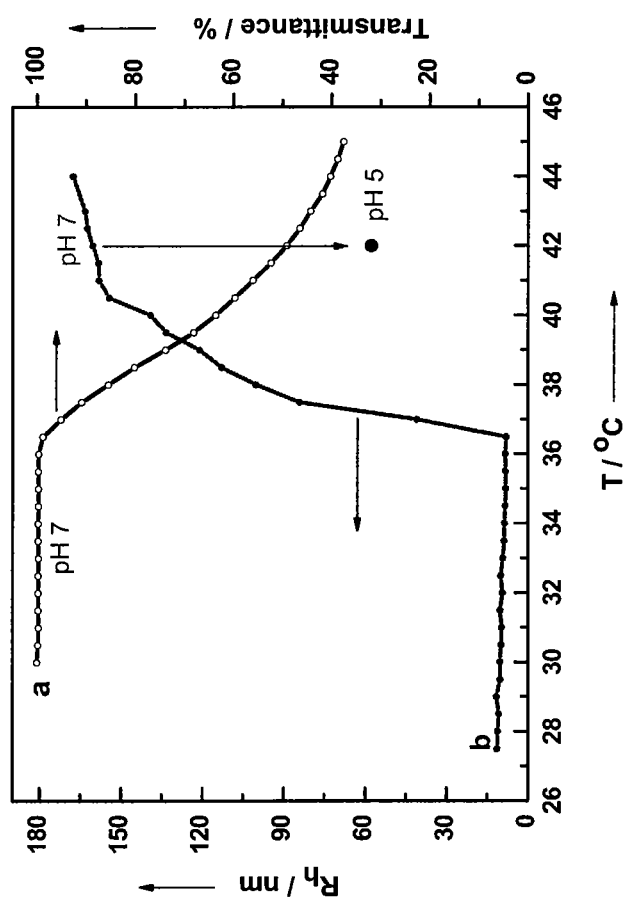
FIG. 13 is a graph showing a) temperature dependence of transmittance of aqueous solution of micelles formed in 1% (w/v) aqueous solution of poly(PEG258DA-AEPZ)-g-NIPAAm$_{0.46}$-g-CEC$_{0.48}$; and b) Effect of temperature and pH on $R_h$ of micelles formed in 0.05% (w/v) aqueous solution of poly(PEG258DA-AEPZ)-g-NIPAAm$_{0.46}$-g-CEC$_{0.48}$.

As shown in FIG. 13, poly(PEG258DA-AEPZ)-g-NIPAAm$_{0.46}$-CEC$_{0.48}$ also exhibits a LCST of 36.5° C., similar to that of poly(PEG258DA-AEPZ)-g-NIPAAm$_{0.46}$. However, the transmittance beyond LCST does not decrease dramatically for amphiphilic poly(PEG258DA-AEPZ)-g-NIPAAm$_{0.46}$-CEC$_{0.48}$, which can be attributed to the formation of micelles in aqueous solution preventing rapid aggregation of polymer particles.

As can be understood by one skilled in the art, many modifications to the exemplary embodiments described herein are possible. The invention, rather, is intended to encompass all such modification within its scope, as defined by the claims.

All documents referred to herein are fully incorporated by reference.

What is claimed is:

1. A stimulus-responsive polymer comprising a biodegradable polymer backbone and a stimulus-responsive pendant group attached to the biodegradable polymer backbone, the stimulus-responsive pendant group being a stimulus-responsive monomer which provides stimulus-responsiveness to the polymer, wherein the biodegradable polymer backbone comprises a poly(amino ester) or a poly(amido amine), the poly(amido amine) optionally comprising a disulfide linkage in the backbone the polymer comprises one or more units each independently selected from a unit of formula I:

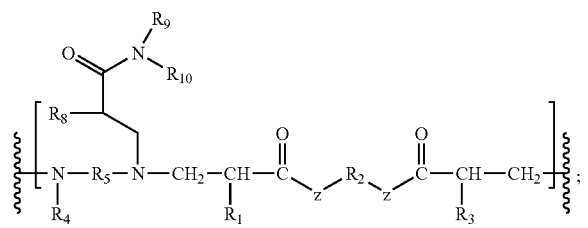

and a unit of formula II:

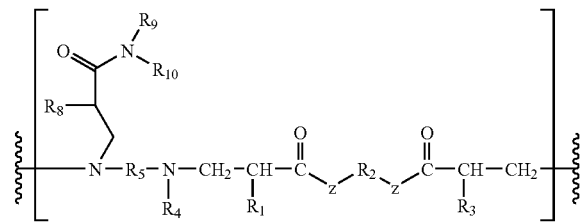

and optionally comprises one or more units, each independently selected from formula III:

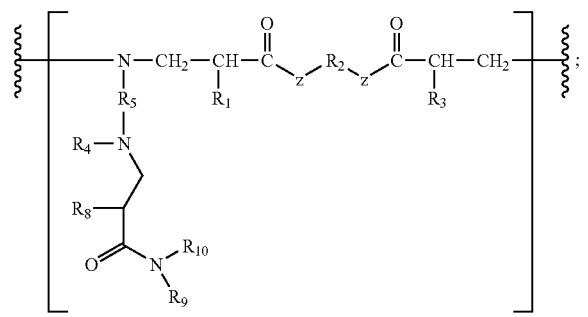

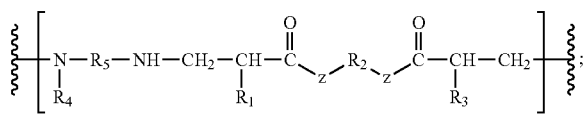

formula IV

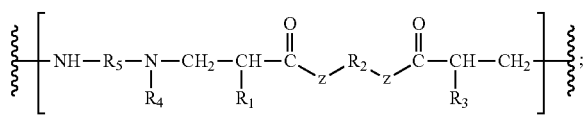

formula V

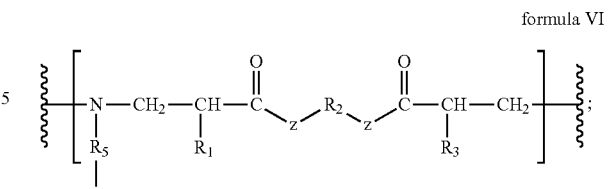

formula VI and

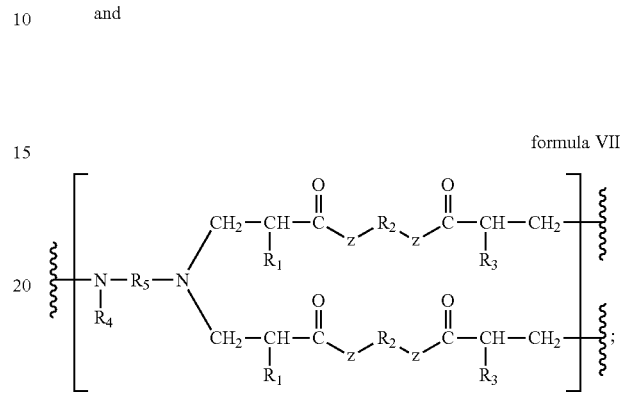

formula VII wherein:

z is O or NH;

each of $R_1$, $R_3$ and $R_8$ is independently hydrogen, hydroxyl, halide, thiohydroxyl or hydrocarbyl;

$R_2$ is unsubstituted or substituted $C_{1-30}$ alkylene optionally containing one or more heteroatoms selected from the group consisting of N, O and S; unsubstituted or substituted $C_{2-30}$ alkenylene optionally containing one or more heteroatoms selected from the group consisting of N, O and S; or unsubstituted or substituted $C_{2-30}$ alkynylene optionally containing one or more heteroatoms selected from the group consisting of N, O and S;

$R_5$ is:
   (i) unsubstituted or substituted $C_{1-30}$ alkylene optionally containing one or more heteroatoms selected from the group consisting of N, O and S; unsubstituted or substituted $C_{2-30}$ alkenylene optionally containing one or more heteroatoms selected from the group consisting of N, O and S; or unsubstituted or substituted $C_{2-30}$ alkynylene optionally containing one or more heteroatoms selected from the group consisting of N, O and S; or
   (ii) —$R_6$-M-$R_7$—, where
      $R_6$ is bonded to —N($R_4$)— and is unsubstituted or substituted $C_{1-6}$ alkylene optionally containing one or more heteroatoms selected from the group consisting of N, O and S, or unsubstituted or substituted $C_{2-6}$ alkenylene optionally containing one or more heteroatoms selected from the group consisting of N, O and S;
      M is CH or N; and
      $R_7$ is unsubstituted or substituted $C_{1-28}$ alkylene optionally containing one or more heteroatoms selected from the group consisting of N, O and S; unsubstituted or substituted $C_{2-28}$ alkenylene optionally containing one or more heteroatoms selected from the group consisting of N, O and S; or unsubstituted or substituted $C_{2-28}$ alkynylene optionally containing one or more heteroatoms selected from the group consisting of N, O and S;

$R_4$ is:
(i) hydrocarbyl; or
(ii) when $R_5$ is —$R_6$-M-$R_7$—, $R_4$ is also bonded to M and is unsubstituted or substituted $C_{1-6}$ alkylene optionally containing one or more heteroatoms selected from the group consisting of N, O and S, or unsubstituted or substituted $C_{2-6}$ alkenylene optionally containing one or more heteroatoms selected from the group consisting of N, O and S; and $R_4$, M, $R_6$ and the nitrogen atom to which $R_4$ and $R_6$ are bonded form a saturated or unsaturated four- to twelve-membered heterocyclic ring, $R_9$ is:
(i) unsubstituted or substituted $C_{1-30}$ alkylene optionally containing one or more heteroatoms selected from the group consisting of N, O and S; unsubstituted or substituted $C_{2-30}$ alkenylene optionally containing one or more heteroatoms selected from the group consisting of N, O and S; or unsubstituted or substituted $C_{2-30}$ alkynylene optionally containing one or more heteroatoms selected from the group consisting of N, O and S; or
(ii) —$R_{11}$-M-$R_{12}$, where
$R_{11}$ is bonded to —N($R_{10}$)— and is unsubstituted or substituted $C_{1-6}$ alkylene optionally containing one or more heteroatoms selected from the group consisting of N, O and S, or unsubstituted or substituted $C_{2-6}$ alkenylene optionally containing one or more heteroatoms selected from the group consisting of N, O and S;
M is CH or N; and
$R_{12}$ is unsubstituted or substituted $C_{1-28}$ alkyl optionally containing one or more heteroatoms selected from the group consisting of N, O and S;
unsubstituted or substituted $C_{2-28}$ alkenyl optionally containing one or more heteroatoms selected from the group consisting of N, O and S; or
unsubstituted or substituted $C_{2-28}$ alkynyl optionally containing one or more heteroatoms selected from the group consisting of N, O and S;

$R_{10}$ is
(i) hydrocarbyl; or
(ii) when $R_9$ is —$R_{11}$-M-$R_{12}$, $R_{10}$ is also bonded to M and is unsubstituted or substituted $C_{1-6}$ alkylene optionally containing one or more heteroatoms selected from the group consisting of N, O and S, or unsubstituted or substituted $C_{2-6}$ alkenylene optionally containing one or more heteroatoms selected from the group consisting of N, O and S; and $R_{10}$, M, $R_{11}$ and the nitrogen atom to which $R_9$ and $R_{11}$ are bonded form a saturated or unsaturated four- to twelve-membered heterocyclic ring;
with the proviso that $R_1$, $R_2$, $R_3$, $R_4$, $R_5$, $R_8$, $R_9$ and $R_{10}$ cannot have a primary amino group, a secondary amino group, or a C=C double bond conjugated with a carbonyl group.

2. The stimulus-responsive polymer according to claim 1 wherein the stimulus-responsive polymer is responsive to pH, light, temperature or ionic strength.

3. The stimulus-responsive polymer according to claim 2 wherein the stimulus-responsive pendant group is a reacted N-isopropylacrylamide, N,N'-diethylacrylamide, 2-carboxylsopropylamide, N-(L)-(1-hydroxymethyl)propylmethacrylamide or N-acryloxyl-N'-alkylpiperazine.

4. The stimulus-responsive polymer according to claim 1, further comprising a hydrophobic pendant group.

5. The stimulus-responsive polymer according to claim 4, wherein the hydrophobic pendant group has a structure of formula XII:

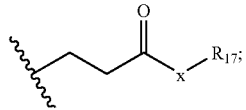

formula XIII:

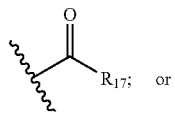

formula XIV:

wherein:
x is O or NH; and
$R_{17}$ is substituted or unsubstituted $C_{3-30}$ alkyl, substituted or unsubstituted $C_{4-30}$ alkenyl, substituted or unsubstituted $C_{4-30}$ alkynyl, substituted or unsubstituted $C_{3-8}$ cycloalkyl, substituted or unsubstituted $C_{6-18}$ aryl, any of which may optionally contain one or more heteroatoms selected from the group consisting of N, O and S.

6. The stimulus-responsive polymer according to claim 4, wherein the hydrophobic pendant group comprises a reacted 4-tert-butylcyclohexyl acrylate, 2-butoxyethyl acrylate, hexyl acrylate, 2-ethylhexyl acrylate, octadecyl acrylate, lauryl acrylate, diacetone acrylamide, N-(butoxymethyl)acrylamide, N-(isobutoxymethyl)acrylamide, cholesteryl chloroformate, nanonoyl chloride, undecanoyl chloride, lauroyl chloride, 4-heptylbenzoyl chloride, myristoyl chloride, 1-bromo-2-cyclohexylethane, 1-bromooctane, 1-adamantyl bromomethyl ketone, 2-bromo-2',5'-dimethyoxyacetophenone, 1-bromo-3,7-dimethyloctane, 1-bromododecane, 1-bromooctane, 1-bromodecane, 1-bromooctadecane, 2-(6-bromohexyloxy)tetrahydro-2H-pyran, 1-iodoadamantane, 1-iodohexane, 1-iodooctane, 1-iododecane, 1-iodododecane or 1-iodooctadecane.

7. A composition comprising a stimulus-responsive polymer as defined in claim 1 and a cross-linking group.

8. The composition according to claim 7 wherein the stimulus-responsive polymer is cross-linked by a cross-linking group having a structure of formula VIII:

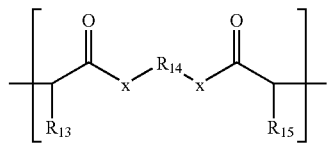

wherein:
x is O or NH;
each of $R_{13}$ and $R_{15}$ is independently hydrogen, hydroxyl, halide, thiohydroxyl or hydrocarbyl; and
$R_{14}$ is unsubstituted or substituted $C_{1-30}$ alkylene optionally containing one or more heteroatoms selected from the group consisting of N, O and S; unsubstituted or substituted $C_{2-30}$ alkenylene optionally containing one or more heteroatoms selected from the group consisting of N, O and S; or unsubstituted or substituted $C_{2-30}$ alkynylene optionally containing one or more heteroatoms selected from the group consisting of N, O and S.

9. The composition according to claim 7 wherein the cross-linking group comprises a cross-linked 1,4-butanediol diacrylate, 1,4-butanediol dimethacrylate, 1,2-ethanediol diacrylate, 1,6-hexanediol diacrylate, 2,5-hexanediol diacrylate, poly(ethyl glycol)diacrylate, ethylene diacrylate, 1,3-propanediol diacrylate, including 1,4-Bis(acryloyl)piperazine, N,N'-Bis(acryloyl)cystamine, N,N'-methylenebisacrylamide, N,N'-(1,2-Dihydroxyethylene)bisacrylamide, 1,3-dibromo-2-propanol, 1,4-dibromo-2-butanol, 1,5-dibromo pentane, 1,6-dibromo hexane, 1,5-diiodo pentane, 1,8-dibromo octane, 1,6-diiodo hexane or 1,8-diiodo octane.

10. A composition comprising a stimulus-responsive biodegradable polymer as defined in claim 1 or a composition as defined in claim 7, and a bioactive agent.

11. The composition according to claim 10 wherein the bioactive agent comprises a small molecule, an organometallic compound, a nucleic acid, a protein, a peptide, a polynucleotide metal, an isotopically labelled chemical compound, a drug, a vaccine, or an immunological agent.

12. The composition according to claim 10 wherein the composition forms a micelle.

13. The composition according to claim 10 wherein the composition forms a hydrogel.

14. A stimulus-responsive polymer comprising a biodegradable polymer backbone and a stimulus-responsive pendant group attached to the biodegradable polymer backbone, the biodegradable polymer backbone comprising a poly(amino ester) or a poly(amido amine), the poly(amido amine) optionally comprising a disulfide linkage in the backbone and the stimulus-responsive pendant group being a stimulus-responsive monomer which provides stimulus-responsiveness to the polymer and being attached to the polymer via a backbone nitrogen and having the structure of formula X:

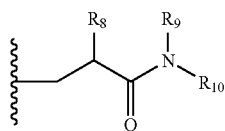

wherein:

$R_8$ is hydrogen, hydroxyl, halide, thiohydroxyl or hydrocarbyl;

$R_9$ is:
 (i) unsubstituted or substituted $C_{1-30}$ alkylene optionally containing one or more heteroatoms selected from the group consisting of N, O and S; unsubstituted or substituted $C_{2-30}$ alkenylene optionally containing one or more heteroatoms selected from the group consisting of N, O and S; or unsubstituted or substituted $C_{2-30}$ alkynylene optionally containing one or more heteroatoms selected from the group consisting of N, O and S; or
 (ii) —$R_{11}$-M-$R_{12}$, where
  $R_{11}$ is bonded to —N($R_{10}$)— and is unsubstituted or substituted $C_{1-6}$ alkylene optionally containing one or more heteroatoms selected from the group consisting of N, O and S, or unsubstituted or substituted $C_{2-6}$ alkenylene optionally containing one or more heteroatoms selected from the group consisting of N, O and S;
  M is CH or N; and
  $R_{12}$ is unsubstituted or substituted $C_{1-28}$ alkyl optionally containing one or more heteroatoms selected from the group consisting of N, O and S;
  unsubstituted or substituted $C_{2-28}$ alkenyl optionally containing one or more heteroatoms selected from the group consisting of N, O and S; or
  unsubstituted or substituted $C_{2-28}$ alkynyl optionally containing one or more heteroatoms selected from the group consisting of N, O and S;

$R_{10}$ is
 (i) hydrocarbyl; or
 (ii) when $R_9$ is —$R_{11}$-M-$R_{12}$, $R_{10}$ is also bonded to M and is unsubstituted or substituted $C_{1-6}$ alkylene optionally containing one or more heteroatoms selected from the group consisting of N, O and S, or unsubstituted or substituted $C_{2-6}$ alkenylene optionally containing one or more heteroatoms selected from the group consisting of N, O and S; and $R_{10}$, M, $R_{11}$ and the nitrogen atom to which $R_9$ and $R_{11}$ are bonded form a saturated or unsaturated four- to twelve-membered heterocyclic ring;

with the proviso that $R_8$, $R_9$ and $R_{10}$ cannot have a primary amino group, a secondary amino group, or a C=C double bond conjugated with a carbonyl group.

* * * * *